(12) United States Patent
Bianchi et al.

(10) Patent No.: US 12,303,370 B2
(45) Date of Patent: *May 20, 2025

(54) ABSORBENT ARTICLE WITH A CHANNEL-FORMING AREA AND A MASKING LAYER

(71) Applicant: The Procter & Gamble Company, Cincinnati, OH (US)

(72) Inventors: Ernesto Gabriel Bianchi, Hessen (DE); Matthias Konrad Hippe, Sulzbach (DE); Aniruddha Chatterjee, Kelkheim (DE); Adrien Grenier, Frankfurt am Main (DE); Andrea Peri, Kronberg (DE); Udo Friedel Schoenborn, Bad Soden (DE); Abhishek Prakash Surushe, Kelkheim (DE)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/655,380

(22) Filed: May 6, 2024

(65) Prior Publication Data

US 2024/0315885 A1 Sep. 26, 2024

Related U.S. Application Data

(63) Continuation of application No. 17/386,086, filed on Jul. 27, 2021, now Pat. No. 12,004,934.

(30) Foreign Application Priority Data

Jul. 30, 2020 (EP) ..................................... 20188705

(51) Int. Cl.
*A61F 13/534* (2006.01)
*A61F 13/15* (2006.01)
(Continued)

(52) U.S. Cl.
CPC ............ *A61F 13/534* (2013.01); *A61F 13/45* (2013.01); *A61F 2013/15373* (2013.01);
(Continued)

(58) Field of Classification Search
CPC ................ A61F 13/45; A61F 13/49007; A61F 13/51496; A61F 13/531; A61F 13/5323;
(Continued)

(56) References Cited

U.S. PATENT DOCUMENTS

| 5,176,672 A | 1/1993 | Bruemmer et al. |
| 12,004,934 B2* | 6/2024 | Bianchi ............... A61F 13/5323 |

(Continued)

FOREIGN PATENT DOCUMENTS

| WO | 00/59430 | * 10/2000 | ............. A61F 13/15 |
| WO | 2012170341 A1 | 12/2012 | |

(Continued)

OTHER PUBLICATIONS

PCT Search Report and Written Opinion for PCT/US2021/042710 dated Nov. 18, 2021, 15 pages.

(Continued)

*Primary Examiner* — Michele M Kidwell
(74) *Attorney, Agent, or Firm* — Christian M. Best

(57) ABSTRACT

An absorbent article comprising a liquid permeable topsheet, a backsheet, an absorbent core comprising an absorbent material and a core wrap is provided. The core comprises at least one channel-forming area that is substantially free of absorbent material. The absorbent article comprises a masking layer between the bottom side of the core wrap and the backsheet. The masking layer and the bottom side of the core wrap are only partially bonded to each other at their interface, the interface thus comprising a bonded portion and an unbonded portion, wherein the channel-forming area at least partially corresponds to the unbonded portion of the (Continued)

interface, so that when the absorbent material swells, the masking layer can decouple from the three-dimensional channels.

20 Claims, 10 Drawing Sheets

(51) Int. Cl.
    *A61F 13/45*     (2006.01)
    *A61F 13/53*     (2006.01)

(52) U.S. Cl.
    CPC ............... *A61F 2013/15959* (2013.01); *A61F 2013/4587* (2013.01); *A61F 2013/530167* (2013.01); *A61F 2013/530868* (2013.01)

(58) Field of Classification Search
    CPC .............. A61F 13/534; A61F 13/53743; A61F 13/5638; A61F 2013/15373; A61F 2013/15959; A61F 2013/4587; A61F 2013/530167; A61F 2013/530868; A61F 2013/5315
    See application file for complete search history.

(56) References Cited

U.S. PATENT DOCUMENTS

| | | |
|---|---|---|
| 2014/0163506 A1 | 6/2014 | Roe |
| 2014/0371701 A1 | 12/2014 | Bianchi |
| 2018/0008479 A1 | 1/2018 | Joseph |
| 2019/0374397 A1 | 12/2019 | Tally et al. |
| 2020/0060891 A1 | 2/2020 | Garcia et al. |
| 2022/0031528 A1 | 2/2022 | Grenier et al. |

FOREIGN PATENT DOCUMENTS

| | | |
|---|---|---|
| WO | 2012170778 A1 | 12/2012 |
| WO | 2013001788 A1 | 1/2013 |
| WO | 2019241009 A1 | 12/2019 |

OTHER PUBLICATIONS

EPO Search Report and Opinion for Application No. 20188705.6; dated Jan. 19, 2021, 8 pages.
All Office Actions; U.S. Appl. No. 17/386,086, filed Jul. 27, 2021.

* cited by examiner

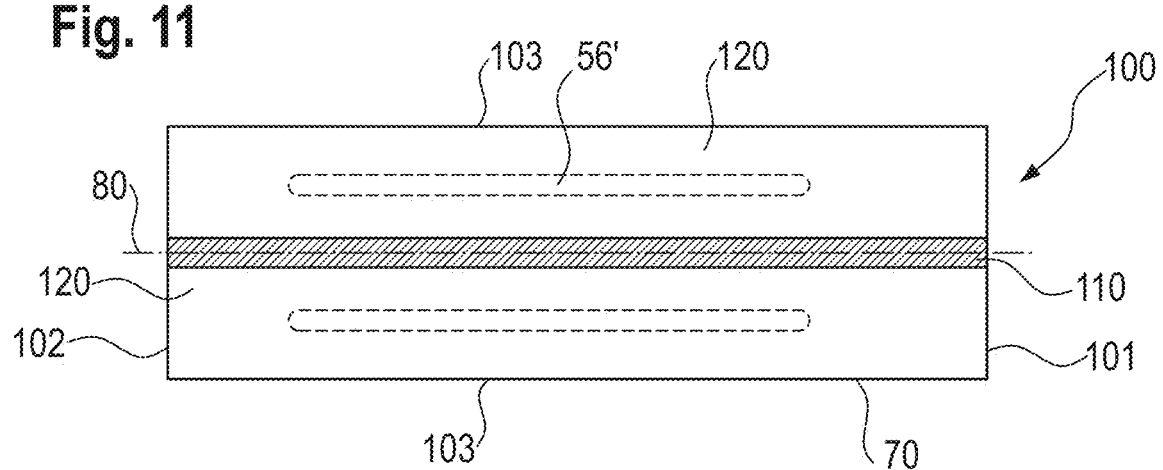
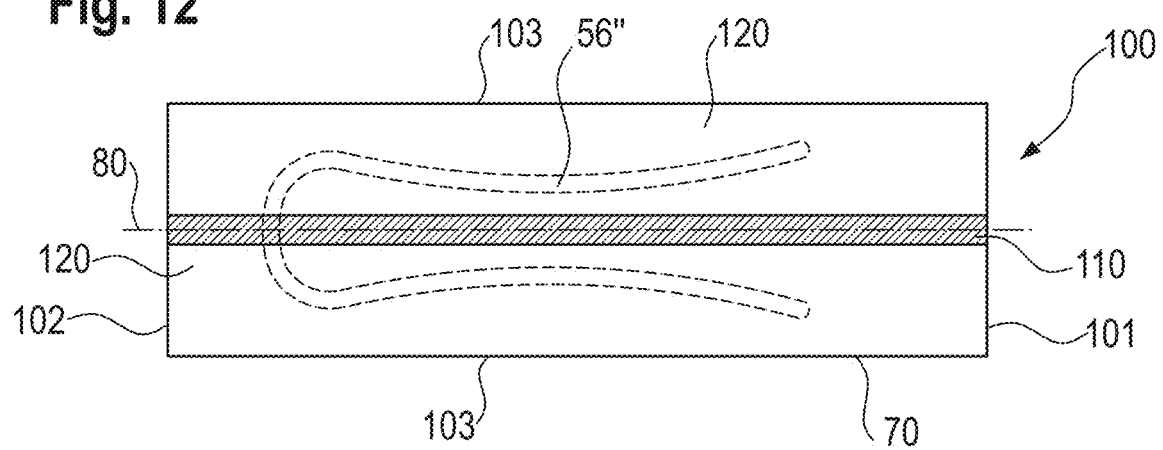

| | Example 1 (prior art) | Example 2 | Example 3 | Example 4 | Example 5 | Example 6 | Example 7 |
|---|---|---|---|---|---|---|---|
| % coverage | 100% | 22% | 22% | 15% | 16% | 29% | 7% |
| Bonding pattern | | | | | | | |

ABSORBENT ARTICLE WITH A CHANNEL-FORMING AREA AND A MASKING LAYER

CROSS REFERENCE TO RELATED APPLICATIONS

This application is a continuation of, and claims priority under 35 U.S.C. § 120 to, U.S. patent application Ser. No. 17/386,086, filed on Jul. 27, 2021, and claims priority, under 35 U.S.C. § 119, to European Patent Application Serial No. EP20188705.6, filed on Jul. 30, 2020, the entire disclosure of both of which are hereby incorporated by reference.

FIELD

The invention relates to personal hygiene absorbent articles such as diapers, comprising at least one channel-forming area in the absorbent core and a masking layer between the backsheet and the absorbent core.

BACKGROUND

Disposable personal hygiene absorbent articles such as baby diapers, training pants and adult incontinence articles are used daily by millions of people for receiving and retaining urine and feces. These absorbent articles generally comprise a liquid pervious topsheet that faces towards the wearer's body, a liquid impervious backsheet that faces externally and an absorbent core interposed between the topsheet and the backsheet. The absorbent core comprises an absorbent material layer typically sandwiched between the top side and bottom side of a core wrap. The core wrap typically comprises a single nonwoven folded over the absorbent material, or two discrete nonwovens layers forming the top side and bottom side of the core wrap respectively and joined at their longitudinal edges. Other common components of such absorbent articles include fluid acquisition and distribution layers, inner and outer barrier leg cuffs, elasticized waistbands, urine indicator, etc . . .

Absorbent cores comprising one or more channel-forming areas, which are areas substantially free of absorbent material within the absorbent material layer and form three-dimensional channels when the absorbent material swells, have been disclosed. The top side and bottom side of the core wrap may be bonded together through these absorbent material-free areas to provide channel bonds. These bonds remain at least partially bonded also in use when the absorbent material swells and thus provide more durable three-dimensional channels. Exemplary disclosures of such absorbent material-free areas can be found in WO2012/170, 778 (Rosati et al.) and US2012/0312,491 (Jackels et al.).

The layers forming the absorbent articles are typically glued to each other over their common surface. WO2012/170341 (Hippe et al.) discloses disposable diapers having absorbent cores attached to the backsheet only in certain attachment zones to reduce see-through and the formation of tension lines on the backsheet. The absorbent core may comprise channel-forming areas outside the attachment zones.

Masking layers disposed at least partially intermediate the absorbent core and the backsheet have been disclosed in some patent publications. U.S. Pat. No. 5,176,672 discloses a diaper or absorbent article comprising a topsheet, a backsheet and an absorbent having a hole therein to receive and isolate bodily waste material from the wearer. An intermediate layer is positioned at the base of the absorbent hole and generally on top of the backsheet. The intermediate layer helps preventing feces from showing through the topsheet. More recently, WO2019/241,009A1 (P&G, Tally et al.) discloses that a masking material may aid in improving the softness of the absorbent material by masking the potentially gritty feel of the superabsorbent material in the absorbent material layer. The masking layer may form the lower substrate of the core wrap or the masking layer may be a discrete layer that is disposed between the core wrap and the backsheet.

It has now been found that the presence of the channels may remain highly visible to the user of the articles through the backsheet even when the backsheet is not attached to the absorbent core in the areas of the channels. The backsheet is typically a low basis weight, highly flexible material than can easily deform and follow the contours of the three-dimensional channels. This may lead the user to believe that the absorbent core is under strain and requires changing, even when the absorbent capacity of the article is still far from being exhausted.

There is therefore a need to effectively conceal the three-dimensional channels in an economic manner from the viewpoint of the backsheet side of the article.

SUMMARY OF THE INVENTION

The present invention is in a first aspect directed to an absorbent article as indicated in the claims, and further detailed in the following description. The absorbent article comprises a liquid permeable topsheet, a backsheet, and an absorbent core comprising an absorbent material sandwiched between a top side and a bottom side of a core wrap. The absorbent core comprises at least one channel-forming area that is substantially free of absorbent material and which forms a three-dimensional channel when the absorbent material in the core swells.

According to the invention, the absorbent article comprises a masking layer between the bottom layer of the core wrap and the backsheet, wherein the masking layer and the bottom layer of the core wrap are only partially bonded to each other. The interface between the masking layer and the core wrap bottom layer thus comprises a bonded portion where the layers are bonded to each other, and a unbonded portion where the masking layer is not bonded to the core wrap. The two layers are preferably adhesively bonded in the bonded portion. The channel-forming area at least partially corresponds to the unbonded portion of the interface, so that when the absorbent material swells, the masking layer can effectively decouple from the three-dimensional channel and thus conceal the channel from the viewpoint of a caregiver examining the backsheet of the article.

The bonded portion may in particular comprise a longitudinally-extending central zone, which at least partially overlaps with the longitudinal centerline of the article. The bonded portion may also comprise one or more corner bond zone(s) or transverse bond zone(s) disposed adjacent any or all of the corners or front and back edges respectively of the interface between the masking layer and the bottom side of the core wrap. This provides for increased transverse flexibility of the article in the crotch region of the article, while providing a stable anchoring of the masking layer at the front and back region of the article.

The masking layer of the invention is particularly useful when the top side and the bottom side of the core wrap are bonded to each other in the channel-forming area(s) as these channel bonds maintain the three-dimensional structure of the channels during a longer use period than non-bonded channels.

The masking layer may have an overall surface which is the same or smaller than the surface of the core wrap. The masking layer may have basis weight at least equal and typically higher than the core wrap layer's basis weight. The masking layer may be advantageously disposed so that it covers selected areas of the absorbent core, in particular the crotch region of the absorbent article, instead of a full coverage of the absorbent core.

According to a further aspect, at least 50% of the surface of the masking layer may be bonded directly or indirectly to the backsheet, especially in area(s) vertically corresponding to the channel-forming area(s).

The partial bonding of the masking layer in addition to providing an improved appearance of the absorbent article, was also found to provide an improved flexibility of the article in the transversal direction.

This and further aspects and advantages of the present invention will be better understood by reference to the following description taken in conjunction with the accompanying drawings. Any preferred and advantageous aspects of the invention described in the following description and drawings is not limiting the scope of the claims unless specifically indicated otherwise.

BRIEF DESCRIPTION OF THE DRAWINGS

FIGS. 6-12 shows alternative bonding patterns and/or channel shapes.

DETAILED DESCRIPTION

Definitions

"Absorbent article" as used herein, refers to personal hygiene products that are placed against or in proximity to the body of a wearer to absorb and contain any exudates discharged from the body. As used herein, the term "body exudates" includes, but is not limited to, urine, blood, vaginal discharges and fecal matter. Absorbent articles include in particular taped and pant baby diapers (herein referred to as diapers), training pants, replaceable inserts that are placed in a washable cover, adult incontinence undergarments, feminine hygiene products, and the like.

"Diaper", as used herein, refers to an absorbent article generally worn by infants and incontinent persons about the lower torso so as to encircle the waist and legs of the wearer and that is specifically adapted to receive and contain urinary and fecal waste. As used herein, term "diaper" includes taped diapers and pant diapers, which is defined below.

"Pant" refers to a disposable article having a pre-formed waist opening and leg openings as in an underwear. A pant is placed in position on the wearer by inserting the wearer's legs into the leg openings and pulling the pant into position about a wearer's lower torso. The pant waist and leg openings are preformed by any suitable techniques including, but not limited to, joining together portions of the article using refastenable and/or non-refastenable bonds (e.g., seam, weld, adhesive, cohesive bond, fastener, etc.). A pant may be preformed anywhere along the circumference of the article (e.g., side fastened, front waist fastened). While the term "pants" is used herein, pants are also commonly referred to as "closed diapers", "prefastened diapers", "pull-on diapers", "training pants", and "diaper-pants".

Figure 1:
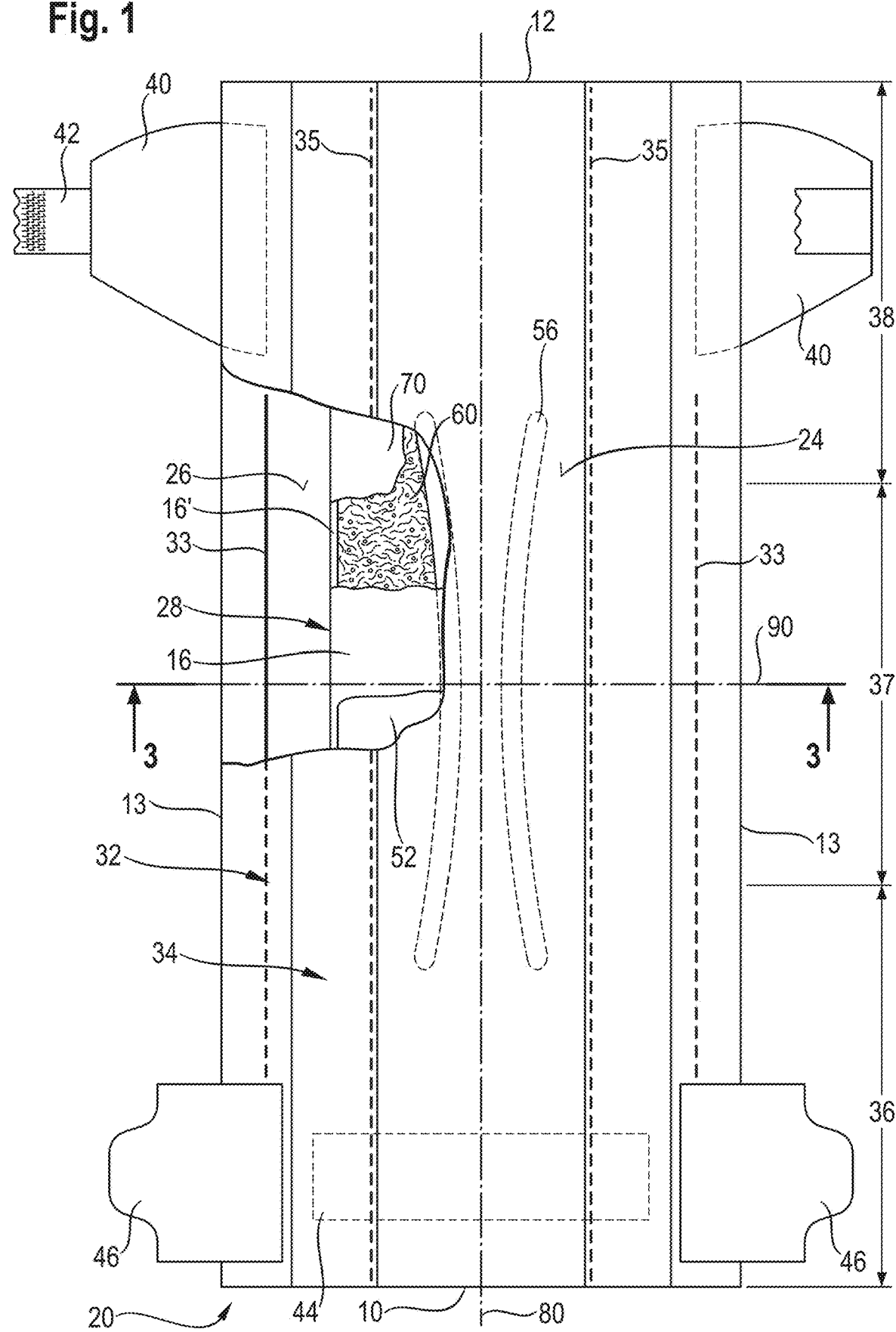
FIG. 1 is a to view of an exemplary absorbent article in the form of a taped diaper, with some layers partially removed to show the interior of the diaper.

"Taped diapers" refer to absorbent articles that comprise fastening tapes, typically in the back half of the product, that can be refastenably attached to a landing zone, typically on the front of the diaper, to form the waist and leg openings. Such a taped diaper is shown in FIG. 1 for example.

"Nonwoven", as used herein, is a manufactured sheet, web, or batt of directionally or randomly orientated fibers, bonded by friction, and/or cohesion and/or adhesion, excluding paper and products which are woven, knitted, tufted, stitch-bonded incorporating binding yarns or filaments, or felted by wet-milling, whether or not additionally needled. The fibers may be of natural or man-made origin and may be staple or continuous filaments or be formed in situ. Commercially available fibers have diameters ranging from less than 0.001 mm to greater than 0.2 mm and they come in several different forms: short fibers (known as staple, or chopped), continuous single fibers (filaments or monofilaments), untwisted bundles of continuous filaments (tow), and twisted bundles of continuous filaments (yarn). Nonwoven fabrics can be formed by many processes such as meltblowing, spunbonding, solvent spinning, electrospinning, and carding. The basis weight of nonwoven fabrics is usually expressed in grams per square meter (gsm).

"Monocomponent" refers to fiber formed of a single polymer component or single blend of polymer components, as distinguished from bicomponent or multicomponent fiber.

"Bicomponent" refers to fibers having a cross-section comprising two discrete polymer components, two discrete blends of polymer components, or one discrete polymer component and one discrete blend of polymer components. "Bicomponent fiber" is encompassed within the term "multicomponent fiber." A bicomponent fiber may have an overall cross section divided into two subsections of the differing components of any shape or arrangement, including, for example, concentric core-and-sheath subsections, eccentric core-and-sheath subsections, side-by-side subsections, radial subsections, etc.

"Multicomponent fiber" includes, but is not limited to, "bicomponent fiber." A multicomponent fiber may have an overall cross section divided into subsections of the differing components of any shape or arrangement, including, for example, coaxial subsections, concentric core-and-sheath subsections, eccentric core-and-sheath subsections, side-by-side subsections, islands-in the sea subsection, segmented pie subsections, etc.

"Substantially", as used herein, means generally the same or uniform but allowing for or having minor fluctuations from a defined property, definition, etc. For example, small measurable or immeasurable fluctuations in a measured property described herein, such as viscosity, melting point, etc. may result from human error or methodology precision. Other fluctuations are caused by inherent variations in the manufacturing process, thermal history of a formulation, and the like. The compositions of the present invention, nonetheless, would be said to be substantially having the property as reported.

"Longitudinal" and "transversal" refer to the direction parallel to the longitudinal centerline 80 and transverse centerline 90, respectively. "Longitudinally-extending" means extending at least twice as much in the longitudinal direction as in the transversal diction, in particular substantially parallel or parallel to the longitudinal centerline. "Transversally-extending" means extending at least twice as much in the transversal direction as in the longitudinal direction, in particular substantially parallel or parallel to the transversal centerline.

General Description of the Exemplary Diaper of FIG. 1

FIG. 1 is a top plan view of an exemplary diaper 20 stretched in a flat-out state with portions of the diaper being cut-away to more clearly show the construction of the diaper. This diaper 20 is shown for illustration purpose only as the structure of the present invention may be comprised in a wide variety of diapers or other absorbent articles, such as pants.

The absorbent article comprises a topsheet 24, a backsheet 26, and an absorbent core comprising a layer of absorbent material 60, which is positioned between the topsheet 24 and the backsheet 26. The liquid-impermeable backsheet 26 prevents the absorbed fluid in the core from leaking out through the garment-facing side of the article. As is known in the art, the backsheet typically comprises a liquid impermeable film for its fluid barrier function, and may optionally have an outer cover nonwoven layer laminated on its external side for providing a softer feel.

Figure 2:
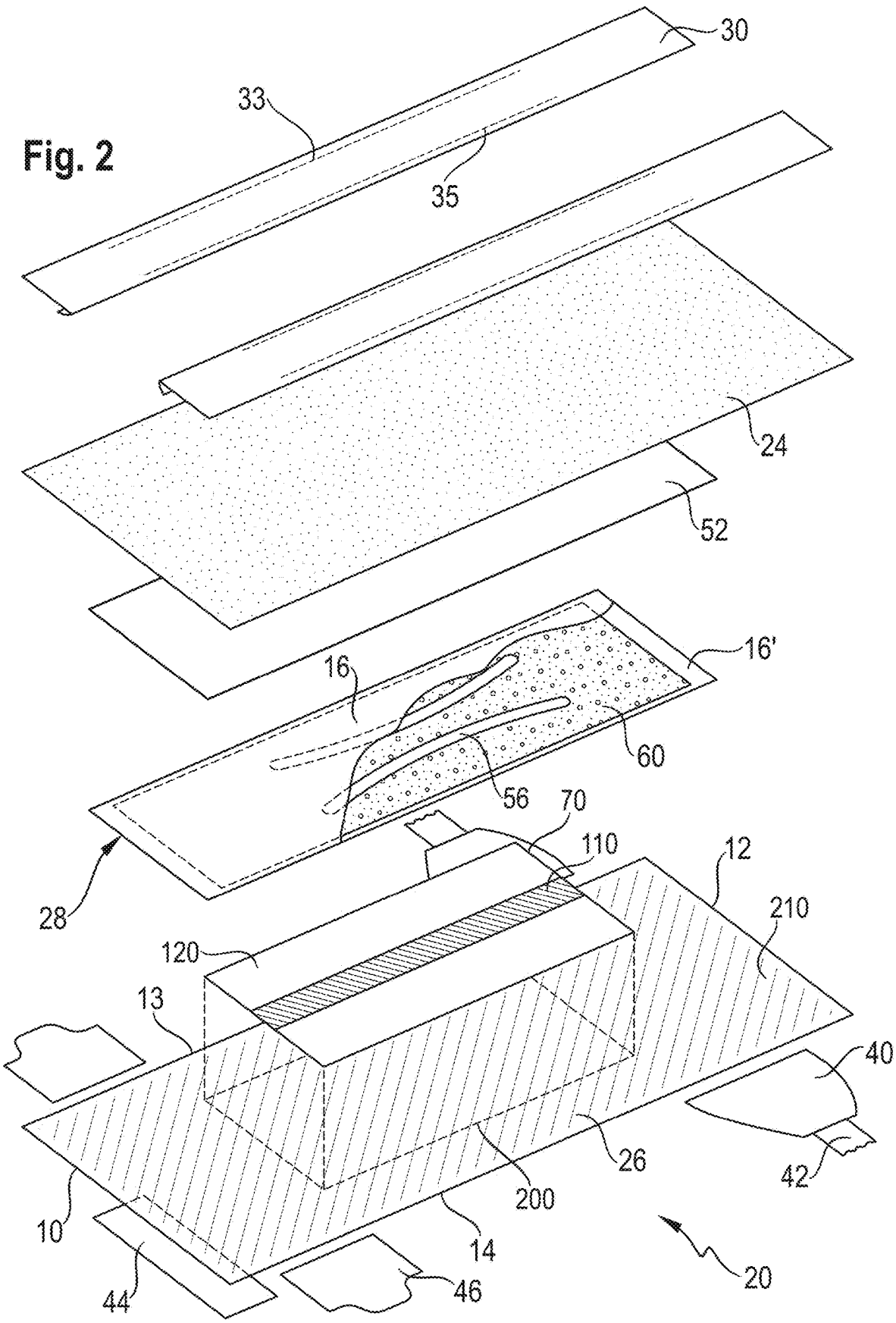
FIG. 2 is an exploded view showing the components of the diaper of FIG. 1.

The absorbent material 60 can absorb and contain liquid received by the absorbent article and is sandwiched between a top side 16 and a bottom side 16' referred herein as core wrap. The core wrap may be made of a single substrate such as a nonwoven or tissue layer, or the top side and bottom side of the core wrap may be each principally formed by a separate substrate layer, as shown in FIG. 2. The absorbent material 60 and the core wrap 16, 16' form together the absorbent core 28. The absorbent article of the present invention further comprises a masking layer 70 disposed between the backsheet 26 and the core wrap's bottom side 16'.

The absorbent article may also comprise upstanding barrier leg cuffs 34 (also referred to as inner leg cuffs) and elasticized gasketing cuffs 32 (also referred to as outer leg cuffs). Moreover, the absorbent article may comprise a fastening system, such as an adhesive fastening system or a hook and loop fastening member, which comprises tape tabs 42 disposed on the back ears 40, such as adhesive tape tabs or tape tabs comprising hook elements, and that can be releasably fastened to a landing zone 44 disposed to the front of the article (e.g. a nonwoven web providing loops in a hook and loop fastening system). Taped diapers also typically comprise front ears 46 that are normally not stretchable, unlike the back ears 40 which are typically, but not necessarily, stretchable. While a taped diaper is represented in FIG. 1, the invention is of course also applicable to pant-type diapers. Of course pant diapers, or more generally pant-type articles have a pre-seamed waist and legs holes so that they do not require a fastening system, as is known in art.

The absorbent article has a longitudinal centerline 80, which is the imaginary line separating the diaper along its length in a left half and right half. The length of the absorbent article is measured along the longitudinal centerline when the absorbent article is laid flat, with all elastic strands hindering a flattened out configuration (such as leg elastics) being cut and thus de-elasticized. Pant articles can be similarly laid flat on a surface after their side seams are opened. The length of the article is adapted for the prospective wearer, for example the length of the article may range from 200 mm to 600 mm. The transversal centerline 90 is the imagery line perpendicular to the longitudinal line 80 in the plane of the flattened-out article and going through the middle of the length of the article. The absorbent article can also be notionally divided in a front waist region 36, a back waist region 38 opposed to the front waist region 36 and a crotch region 37 located between the front waist region 36 and the back waist region 38. The front, back and waist regions have the same length in the longitudinal direction. The crotch region, the first and the second waist regions each constitutes ⅓ of the absorbent article along the longitudinal centerline. The periphery of the diaper 20 is defined by the outer edges of the diaper. The longitudinal edges 13 of the diaper may run generally parallel to the longitudinal centerline 80 of the diaper 20 and the front waist edge 10 and the back waist edge 12 run between the longitudinal edges generally parallel to the transversal centerline 90.

The front ears 46 and/or the back ears 40 may be separate components attached to the chassis of the absorbent article or may instead be formed from portions of the topsheet and/or backsheet such that these portions form all or a part of the front and/or back ears. Also combinations of the aforementioned are possible, such that the front and/or back ears 46, 40 are formed by portions of the topsheet and/or backsheet while additional materials are attached to form the overall front and/or back ears.

The topsheet 24 is the part of the absorbent article 20 that is in contact with the wearer's skin. The topsheet is liquid permeable, permitting liquid bodily exudates to readily penetrate through its thickness. Typical topsheet are manufactured from nonwoven material or apertured plastic films and may comprise synthetic of natural fibers (e.g., wood or cotton fibers). The topsheet may be apertured or non-apertured, and may have any suitable three-dimensional features, and/or may have a plurality of embossments (e.g., a bond pattern). Any portion of the topsheet may be coated with a skin care composition, an antibacterial agent, a surfactant, and/or other beneficial agents. The topsheet may be hydrophilic or hydrophobic or may have hydrophilic and/or hydrophobic portions or layers. If the topsheet is hydrophobic, typically apertures will be present so that bodily exudates may pass through the topsheet.

The backsheet generally constitutes all or a part of the garment-facing side of the absorbent article. The backsheet prevents, or at least inhibits, the bodily exudates absorbed and contained in the layer of absorbent material 60 from soiling articles such as bedsheets, undergarments, and/or clothing. The backsheet 26 typically comprises a liquid impermeable film 26 and optionally an outer nonwoven cover laminated thereto. Such as a thermoplastic film may typically have a thickness of about 0.01 mm to about 0.1 mm. The plastic film may be breathable, and permit vapors to escape from the absorbent article, while still preventing bodily exudates from passing through the backsheet, as is known in the art. A breathable backsheet may have an air permeability greater than 150 $m^3/m^2/min$, or from 200 $m^3/m^2/min$ to 800 $m^3/m^2/min$, as determined by the Air Permeability Test Method set out below.

The backsheet may also comprise an outer cover which is a nonwoven material adhesively laminated to the backsheet 26, and which covers the garment-facing side of the backsheet. The backsheet outer cover nonwoven may comprise a bond pattern, apertures, and/or three-dimensional features, as is known in the art. These backsheet outer cover typically cover the entirety of the backsheet and have a relatively low basis weight of less than 20 $g/m^2$, e.g. from 6 $g/m^2$ to 16 $g/m^2$. In some diapers, the front and back side of the diaper is not sealed so that the user can access to the inner side of the backsheet. These diapers may also comprise an inner nonwoven cover which is a nonwoven laminated to the backsheet on the internal side of the backsheet. These backsheet outer cover typically cover almost the entirety of the backsheet to which they are fully glued and have a relatively low basis weight of less than 20 $g/m^2$, e.g. from 6 $g/m^2$ to 16 $g/m^2$ and are considered as part of the backsheet and not a masking layer according to the invention.

Absorbent articles typically comprise a fluid acquisition layer 52 or a fluid acquisition system comprising several layers between the topsheet and the absorbent core. The fluid acquisition layer may be a nonwoven material that can quickly pull a fluid from the topsheet and redistribute to the absorbent core. The acquisition layer may have any suitable size, and may be smaller, larger or same size as the absorbent material layer 60 of the absorbent core 28 (as considered when the diaper is flattened out as in FIG. 1). The acquisition layer is typically hydrophilic, as defined by a contact angle with deionized water at 22° C. of less than 90°, typically a contact angle of less than 70°. A typical acquisition layer is in particular an air-through bonded carded nonwoven, for example having a basis weight of from 20 gsm to 100 gsm, alternatively from 30 gsm to 80 gsm. Such acquisition layer is typically made of synthetic fibers that have been hydrophillically treated with a surfactant, as is known in the art. The absorbent article may also comprise an additional distribution layer (not represented) between the acquisition layer 52 and the top side 16 of the absorbent core, for example a layer of cross-linked cellulose fibers or spunlace material as is known in the art.

Any components of the disposable absorbent article (i.e., diaper, pant, sanitary napkin, pantiliner, etc.) of the present invention can at least partially be comprised of bio-sourced content as described in US2007/0219521A1, US2011/0139658A1, US2011/0139657A1, US2011/0152812A1, US2011/0139662A1 and US2011/0139659A1 (all Hird et al.). These components include, but are not limited to, topsheet nonwovens, backsheet films, backsheet nonwovens, barrier leg cuff nonwovens, superabsorbent material, upper and lower substrate layer, adhesives, fastener hooks, and fastener landing zone nonwovens and film based.

Further, the absorbent article may comprise other known elements, such as a front and/or back elasticized waistband, a lotion applied onto the body-facing surface of the topsheet, a urine indicator etc . . . all these components have been described and exemplified in the art and are not further detailed herein. More detailed disclosures of example of such components are for example disclosed in WO2014/93323, WO2015/183669 (both Bianchi et al), WO 2015/031225 (Roe et al.) or WO2016/133712 (Ehrnsperger et al.) to name a few. Pant-type articles comprise a central chassis and elasticized front waist and back waist belts. The belts typically comprise transversally extending elastic strands sandwiched between two nonwoven layers, as is known in the art. The chassis comprises a topsheet, absorbent core and backsheet, and according to the invention a masking layer, which may be in a similar construction as described herein for the taped diaper.

A plurality of absorbent articles are typically packaged for transport and sale in bags or boxes, optionally under compression. The packages may optionally have an In Bag Stack Height (i.e. the total caliper of 10 optionally bi-folded articles) of from 70 mm to 110 mm.

The topsheet 24, the backsheet 26, the absorbent core 28, and other article components may be assembled in a variety of well-known configurations, in particular by gluing, fusion and/or pressure bonding. A more detailed description of some components of the absorbent article will now follow.

Absorbent Core 28

The absorbent core 28 comprises an absorbent material 60 and is the component of the absorbent article having the most absorbent capacity. The absorbent layer formed by the absorbent material 60 can have any shape, such as being generally rectangular or non-rectangular, for example sand-hour shaped with a tapering along its width towards the middle region of the core (when seen from the top, as illustrated in FIG. 1). In this way, the absorbent layer may have a relatively narrow width in an area of the core intended to be placed in the crotch region of the absorbent article. This may provide for example better wearing comfort. Other shapes can also be used such as rectangular, a "T" or "Y" or "dog-bone" shape for the area of the absorbent material. This is of course not limiting the scope of the invention as the invention is applicable to a wide variety of absorbent cores.

Figure 3:
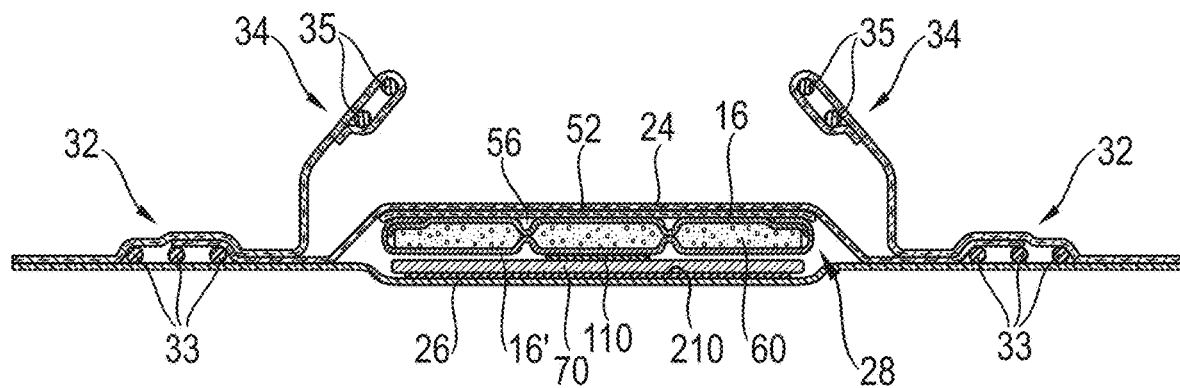
FIG. 3 is a transversal cross-section of the diaper of FIG. 1 when dry.

When two substrates 16, 16' are used to form the core wrap, these may be attached to each other at least longitudinally, for example as a C-wrap as illustrated in FIG. 3 (the longitudinal seals such as glue bonding are not represented for simplicity). Typically, the core wrap is generally rectangular, as seen from the top, even when the absorbent layer sandwiched therebetween is non-rectangular.

The absorbent material 60 may be any conventional absorbent material known in the art. For example, the absorbent material may comprise a blend of cellulose fibers and superabsorbent particles ("SAP"), typically with the percentage of SAP ranging from 40% to 75% by weight of the absorbent material. The absorbent material layer 60 may advantageously also be free of cellulose fibers, as is known in so-called airfelt-free cores where the absorbent material consists of SAP. Airfelt-free cores are typically much thinner compared to conventional cellulose fibers comprising cores, and may thus be particularly useful when combined with an acquisition layer made of a nonwoven according to the present invention.

"Superabsorbent polymers" or "SAP" as used herein refer to absorbent material which are cross-linked polymeric materials that can absorb at least 10 times, preferably at least 15 times, their weight of an aqueous 0.9% saline solution as measured using the Centrifuge Retention Capacity (CRC) test (EDANA method NWSP 2410R2 (19)). These polymers are typically used in particulate forms so as to be flowable in the dry state. The term "particles" refers to granules, fibers, flakes, spheres, powders, platelets and other shapes and forms known to persons skilled in the art of superabsorbent polymer particles.

Various absorbent core designs comprising high amount of SAP have been proposed in the past, see for example in U.S. Pat. No. 5,599,335 (Goldman), EP1,447,066 (Busam), WO95/11652 (Tanzer), US2008/0312622A1 (Hundorf), WO2012/052172 (Van Malderen). In particular the SAP printing technology as disclosed in US2006/024433 (Blessing), US2008/0312617 and US2010/0051166A1 (both to Hundorf et al.) may be used. The invention is however not limited to a particular type of absorbent core. The absorbent core may also comprise one or more glue such as auxiliary glue applied between the internal surface of one (or both) of the core wrap layers and the absorbent material to reduce leakage of SAP outside the core wrap. A micro-fibrous adhesive net may also be used in air-felt free cores, as described in the above Hundorf references. These glues are not represented in the Figures for simplicity.

The absorbent material may be for example deposited as a continuous layer between the top side 16 and the bottom side 16' of the core wrap. The core wrap is typically comprised of a nonwoven with a basis weight between 6 g/m$^2$ to 25 g/m$^2$, preferably between 8 g/m$^2$ and 20 g/m$^2$. The core wrap may comprise a SMS material (spunbond-meltblown-spunbond laminate).

The absorbent material may also be present discontinuously for example as individual pockets or stripes of absorbent material enclosed within the core wrap and separated from each other by material-free junction areas. A continuous layer of absorbent material, in particular of SAP, may also be obtained by combining two absorbent layers having matching discontinuous absorbent material application pattern wherein the resulting layer is substantially continuously distributed across the absorbent particulate polymer material area. As for example taught in US2008/312,622A1 (Hundorf), each absorbent material layer may thus comprise a pattern having absorbent material land areas and absorbent material-free junction areas, wherein the absorbent material land areas of the first layer correspond substantially to the absorbent material-free junction areas of the second layer and vice versa.

Alternatively, the absorbent article may comprise a high loft absorbent core (not shown in the Figure). Such absorbent cores comprises a fluid-permeable top layer, a bottom layer and a central layer between the top layer and the bottom layer, wherein the central layer is or comprises a high loft fibrous nonwoven layer, so that the superabsorbent particles are at least partially distributed within the pores of the high loft nonwoven layer. The high loft nonwoven can be for example a carded web comprising synthetic fibers having a basis weight of from 10 gsm to 100 gsm. Examples of such high loft cores are disclosed in WO2016/106,021A1 (Bianchi et al., P&G). The top layer and bottom layer may be a nonwoven or a tissue layer and form the core wrap of the absorbent core. The absorbent core may also comprise a further layer forming an overwrap (typically C-wrap), such as nonwoven (SMS or other) around the top, central and bottom layers, in which case this overwrap forms the core wrap of the absorbent core.

The basis weight (amount deposited per unit of surface) of the absorbent material may also be varied to create a profiled distribution of absorbent material, in particular in the longitudinal direction to provide more absorbency towards the center and the middle of the core, but also in the transversal direction, or both directions of the core.

Figure 4:
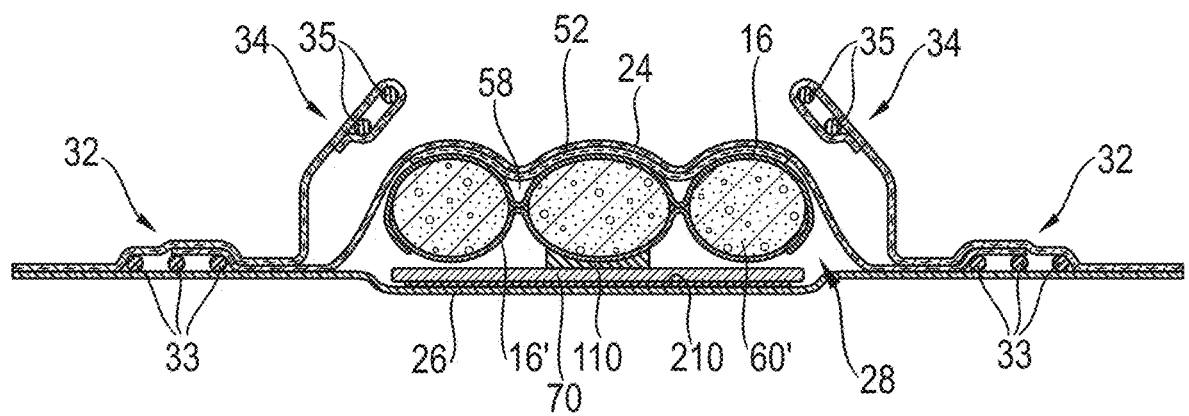
FIG. 4 schematically shows the same cross-section after the core has absorbed a liquid.

The absorbent core comprises one or more channel-forming area(s) 56, which are areas substantially free of absorbent material and at least partially surrounded by absorbent material. In the following, the plural form "areas" means "one or more areas" for simplicity, unless specifically indicated otherwise. The top side of the core wrap may be bonded to the bottom side through these absorbent material-free areas to provide permanent or semi-permanent channel bonds. These bonds at least partially remain bonded also in use when the absorbent material swells and thus provide more durable three-dimensional channels. Permanent channel bonds in particular remain substantially intact up to saturation of the absorbent core with urine. This is for example illustrated on FIG. 4, where the channels 58 surrounded by the swollen absorbent material are shown. Exemplary disclosures of such absorbent material-free areas can be found in WO2012/170,778 (Rosati et al.) and US2012/031,2491 (Jackels et al.). At least some of the channel-forming areas may have a length as measured in the longitudinal direction which is at least 10% of the length L of the article, in particular from 15% to 80% of the length L of the article. The channel-forming areas are typically at least present in the crotch region of the article 37. The channel-forming areas may extend from the crotch region 37 into the front region 36, or into the back region 38, or into both front region 36 and back region 38. At least one or more channel-forming areas may extend longitudinally from the crotch region 37 of the article into the back region 38 and front region 36. The channel-forming areas may also comprise front channel-forming areas present in the front region in addition to central channel-forming areas present in the crotch region.

Channels can improve the flexibility of the articles, in particular in the transversal direction, as well as the speed of acquisition of the speed in the core as they can transport fluid quickly towards the front and back of the core.

The channel-forming areas 56 can have any shape. The channel-forming areas may be curved (e.g. as illustrated in FIGS. 1-10,12), or may be straight (e.g. as illustrated in FIG. 11), or may be partially curved and partially straight, or have a U shape (e.g. as illustrated in FIG. 12, or a peanut or dog-bone shape etc. various examples of channel-forming areas are for example disclosed in WO2018/210,752A1 and WO2018/210,754A1 (both to Drylock).

The absorbent article of the invention comprises a masking layer 70 disposed between the bottom side 16' of the core wrap and the backsheet 26. The masking layer may be a single layer or a laminate of two or more layers of laminates. Desirable properties for such masking layer, as well as the bonding pattern of the masking layer to the absorbent core are discussed further below.

Masking Layer 70

The absorbent article comprises an intermediate masking layer 70 disposed between the absorbent core 28 and the backsheet 26. The intermediate layer is typically a nonwoven material but other materials such as a film, a foam, or any other suitable material are not excluded. The masking layer at least partially conceals the three-dimensional channels formed as the absorbent material swells as seen from the backsheet of the article.

The masking layer may also have further benefits such as isolating the SAP particles of the absorbent layer from the backsheet, thus improving the tactile properties of the garment-facing side of the article, especially for absorbent cores free of cellulose fibers. Examples of masking layer material are disclosed in WO2019/241,009A1 (P&G, Tally et al.)

The masking layer may also be useful to further isolate the exudates which have been absorbed in the absorbent core from the garment-facing side of the article, as this may be visually unpleasant to the caregiver. Thus by having a masking layer with a relatively high opacity, stains in the layer of absorbent material (e.g. from urine or feces) can be concealed from view, when looking at the backsheet of the absorbent article during use. The dry opacity of the masking layer may be at least 25%, or at least 40%, or at least 50%, or at least 70% as measured according to the Opacity Test method set out below. The masking layer can also help reducing the residual moisture in contact with the backsheet, which lead to cold/wet feeling for the caregiver and the wearer sometime mistakenly taken as liquid leaking out of the absorbent article.

Finally the masking layer may also have fluid acquisition and/or distribution properties, for example to acquire and re-distribute absorb any gush of fluids that could not be directly absorbed by the absorbent core. Of course a masking layer according to the invention does not need to have all or any of the further properties or function indicated previously.

The masking layer may be a relatively lofty material (typically a nonwoven such as a spunlace, an air-through bonded nonwoven, a carded calendar bonded nonwoven, or a spunbond or carded nonwoven comprising crimped fibers), providing sufficient void volume to separate the absorbent core 28 from the garment-facing side of the article. The masking layer is preferably a discrete layer, which may be a homogeneous layer or an integrated layer comprising integrated precursor webs, for example as is known in the art for spunlace.

In a spunlace nonwoven the fibers have been subjected to hydroentanglement to intermingle and intertwine the fibers with each other. Cohesion and the interlacing of the fibers with one another may be obtained by means of a plurality of jets of water under pressure passing through a moving fleece or cloth and, like needles, causing the fibers to intermingle with one another. Thus, consolidation of a spunlace nonwoven web is essentially a result of hydraulic interlacing. "Spunlace nonwoven", as used herein, also relates to a nonwoven formed of two or more precursor webs, which are combined with each other by hydraulic interlacing. The two or more webs, prior to being combined into one nonwoven by hydraulic interlacing, may have underdone bonding processes, such as heat and/or pressure bonding by using e.g. a patterned calendar roll and an anvil roll to impart a bonding pattern. However, the two or more webs are combined with each other solely by hydraulic interlacing. Alternatively, the spunlace nonwoven web is a single web, i.e. it is not formed of two or more precursor webs. Spunlace nonwoven layers/webs can be made of staple fibers or continuous fibers.

Through-air bonding (interchangeably used with the term "air through bonding") means a process of bonding staple fibers or continuous fibers by forcing air through the nonwoven web, wherein the air is sufficiently hot to melt (or at least partly melt, or melt to a state where the fiber surface becomes sufficiently tacky) the polymer of a fiber or, if the fibers are multicomponent fibers, wherein the air is sufficiently hot to melt (or at least partly melt, or melt to a state where the fiber surface becomes sufficiently tacky) one of the polymers of which the fibers of the nonwoven web are made. The air velocity is typically between 30 and 90 meter per minute and the dwell time may be as long as 6 seconds. The melting and re-solidification of the polymer provide the bonding between different fibers. The through-air bonded web may in particular be an air through bonded carded web.

Typically, the thickness of the masking layer should be large enough to provide the desired masking effect, while having a low enough stiffness to allow the absorbent article to remain flexible and conform to a wearer. The masking layer may thus have a thickness (C1) of from 0.2 mm to 4.00 mm, preferably of from 0.35 mm to 2.00 mm, as measured at a pressure of 0.85 kPa according to the Z-Compliance Index and Percent Recovery Measurement Method described herein.

The basis weight of the masking layer may be homogeneous along the length and width of the masking layer (i.e. in the longitudinal and transverse direction). The masking layer may advantageously have a basis weight ranging of from about 20 grams per square meter (gsm) to about 150 gsm, preferably from 25 gsm to 100 gsm, or from 30 gsm to 80 gsm. The masking layer typically has a higher basis weight than the layer forming the core wrap's bottom side. Of course local basis weight variations on a rather small scale (such as variations within 1.0 cm, or within 0.5 cm in width and length direction) may also exist for layer of homogenous basis weight, which may result from mechanical deformation of the masking layer for example. The masking layer may optionally be a mechanically deformed nonwoven having three-dimensional features. Such mechanical deformation can contribute to the loft and openness of the nonwoven web. Examples of mechanical deformation process are for example disclosed in WO2012/148, 944A1 and WO2016/040101. Suitable deformation processes cause fibers from the nonwoven to protrude from one or both sides of the nonwoven to form discrete protrusions, as exemplified in these documents.

The masking layer may be smaller in the longitudinal direction and/or transverse direction than the absorbent core, so that the lower layer of the core wrap is extending beyond the masking layer in longitudinal and/or transverse direction. The masking layer may be typically shorter in the longitudinal direction than the absorbent core, as the front and back of the core typically comprise less SAP and are less compressed by the legs of the wearer than the crotch region of the core.

The masking layer is typically free of superabsorbent polymer if it is used as a masking layer or a lower distribution layer. If it used as a secondary storage layer, it may comprise some superabsorbent polymers, or alternatively absorbent fibers such as cellulose fibers.

The masking layer may be a nonwoven comprising fibers of natural or man-made origin. Natural fibers may be selected from the group consisting of wheat straw fibers, rice straw fibers, flax fibers, bamboo fibers, cotton fibers, jute fibers, hemp fibers, sisal fibers, bagasse fibers, Hesper aloe fibers, miscanthus, marine or fresh water algae/seaweeds, silk fibers, and combinations thereof. Preferably, the natural fibers are selected from the group consisting of cotton fibers, bamboo fibers, or mixtures thereof. Preferably, the natural fibers are cotton fibers. Synthetic fibers may be selected from the group consisting of polyolefins (such as polyethylene, polypropylene or combinations and mixtures thereof), polyethylene terephthalate (PET), co PET, polylactic acid (PLA), polyhydroxy alkanoid (PHA), or mixtures or combinations thereof.

The fibers may be continuous or staple fibers. The fibers may be monocomponent fibers or multicomponent fibers, such as bicomponent fibers. If the fibers comprised by the masking layer are bicomponent fibers, they may have a core-sheath configuration, wherein the core component has a higher melting point than the sheath component. They may also have side by side configuration, so that one side of fiber has more retraction properties then the other side to allow crimping of the fibers.

The masking layer may also have advantageously a Z-Compliance Index of at least 10 mm$^3$/N, preferably at least 15 mm$^3$/N, as measured according to the Z-Compliance Index and Percent Recovery Measurement Method described herein. Higher values such as those for the mechanically deformed nonwovens can of course be advantageous, the masking layer thus can have a Z-Compliance Index of at least 50 mm$^3$/N, or even at least 60 mm$^3$/N, as measured according to the Z-Compliance Index and Percent Recovery Measurement Method described herein.

The masking layer 70 may have an air permeability greater than 150 m$^3$/m$^2$/min, or from 200 m$^3$/m$^2$/min to 800 m$^3$/m$^2$/min, as determined by the Air Permeability test method set out below.

The masking layer may optionally be hydrophobic, so as to have a barrier function between the absorbent layer and the backsheet. The masking layer may thus have a contact angle with deionized water at 22° C. of more than 90°, typically a contact angle of more than 100°. The contact angle may be more easily measured on the precursor nonwoven if the masking layer is mechanically deformed.

The masking layer may optionally have a Horizontal Bending Drop at 100 mm of at least 20 mm, or at least 40 mm, or at least 60 mm, as measured in the longitudinal direction as indicated in the Horizontal Bending Drop at 100 mm Measurement Method described below. Higher values correspond to more drapable materials and may be advantageous.

Mechanically deforming a nonwoven as disclosed above typically increased these values for a given material. The masking layer may thus also have Horizontal Bending Drop of at least 75 mm, or at least 80 mm, or at least 85 mm, as measured with the Horizontal Bending Drop at 100 mm Measurement Method described herein.

Examples of Masking layer

Here below are some non-limiting examples of material that are suitable as masking layers.

Option 1: Carded air through bonded nonwoven web made of 60 weight-% of CoPET/PET solid round bicomponent (core/sheath) staple fibers of 2.2 dtex and 40 weight-% of PET solid round monocomponent staple fibers of 3.3 dtex. The material has a basis weight of 30 g/m$^2$.

Option 2: Carded air through bonded nonwoven web made of 100% polyethylene/PET solid round bicomponent (core/sheath) staple fibers of 4.4 dtex. The material has a basis weight of 60 g/m$^2$.

Option 3: Air through bonded nonwoven web made of 60 weight % of CoPET/PET solid round bicomponent (core/sheath) staple fibers of 2.2 dtex and 40 weight-% of PET solid round monocomponent staple fibers of 3.3 dtex. The material has a basis weight of 60 g/m$^2$.

Option 4: Hydroentangled nonwoven web with 30 weight-% viscose fibers and 70 weight-% polyester fibers. The nonwoven web has a basis weight of 40 g/m$^2$.

Option 5: Nonwoven web made of 100% monocomponent PP with SMS layers. The spunbond ("S") layer has fibers of 2.2 dtex and the meltblown ("M") layer has fiber diameter lower than 2 microns. The meltblown layer has a basis weight of 1.8 g/m$^2$ and the spunbond layers each have a basis weight of 9.1 g/m$^2$. The nonwoven web has a basis weight of 20 g/m$^2$.

Option 6: Spunbonded nonwoven web, made of crimped PP/PP fibers. The nonwoven is hydroentangled. The web has a basis weight of 35 g/m$^2$.

Option 7: Spunbonded nonwoven web, made of crimped PP/PP fibers. The nonwoven is hydroentangled. The web has a basis weight of 55 g/m$^2$.

Option 8: Carded air through bonded nonwoven web made of 60 weight-% of CoPET/PET solid round bicomponent (core/sheath) staple fibers of 2.2 dtex and 40 weight-% of PET solid round mono-component staple fibers of 3.3 dtex.

Option 9: Carded air through bonded nonwoven web made of 100% bicomponent PE/PET (core sheath) fibers of 2.2 dtex.

Option 10: Spunlace with 20 weight % of Viscose and 80 weight % of mono-component PET fibers.

Option 11: Carded calendar bonded material made of 2 layers. Layer one is made of 70 weight % PET fibers of 6.7 dtex and 30 weight % PP fibers of 2.2 dtex (30 g/m$^2$). Layer 2 is made of 100 weight % of PP fibers Option 12:24 gsm Highloft SSS (i.e. 3 spunbond layers) Spunlaid with crimped bicomponent PP/PP fibers The properties of some of these options and other suitable materials are indicated in the table below.

| Material | Basis weight [g/m$^2$] | Dry Opacity [%] | Air permeabiltiy [m$^3$/m$^2$/min] | Horizontal Bending Drop at 100 mm [mm] | Percentage Recovery [%] | Z-Compliance Index | Caliper [2.1 kPA] |
|---|---|---|---|---|---|---|---|
| Option 1 | 30 | 27 | 485 | 92 | 75.1 | 11.7 | 0.28 |
| Option 2 | 60 | 66 | 269 | 66 | 59.1 | 31.8 | 0.44 |
| option 5 | 20 | 29 | 172 | 93 | 83 | 4.3 | 0.11 |
| Option 8 | 45 | 34 | 342 | 75 | 82.7 | 13.4 | 0.33 |
| Option 9 | 20 | 36 | 489 | 89 | 65 | 9.6 | 0.12 |
| Option 10 | 40 | 52 | 236 | n.a | n.a | n.a | 0.34 |
| Option 11 | 40 | 33 | 310 | 92 | 58.5 | 30 | 0.42 |
| Option 12 | 24 | 36 | 252 | 97 | 74.6 | 7.1 | 0.17 |

Bonding Pattern Between the Masking Layer and the Core Wrap

The masking layer is a substantially planar layer having a first surface oriented towards to the topsheet (herein wearer-facing side) and a second opposed surface oriented towards the backsheet (herein garment-facing side). According to the present invention, it was found that the masking layer 70 and the bottom side 16' of the core wrap (herein referred to as "core wrap bottom side" or "bottom side" for simplicity) should be only partially bonded to each other at their interface 100. The interface 100 is the common surface between these two layers. When the masking layer 70 does not extend beyond the core wrap 16, as is typically the case and as represented in the drawings, the interface 100 corresponds to the wearer-facing surface of the masking layer 70. However it is not excluded that the masking layer may also be longer and/or larger than the core wrap, even partially, in which case the interface would have a different, smaller outline than the masking layer 70.

The interface has a bonded portion and a unbonded portion between the two layers. The masking layer can at least partially decouple from the from the bottom side of the core wrap in the unbonded portion. The bonded portion may be a single zone such as a longitudinally-extending stripe, or it may comprise several discrete bonding zones which are not necessarily connected, as will be discussed below with reference to the various examples in the Figures. Likewise, the unbonded portion may be a single area, but it may also comprise several unbonded areas which are also not necessarily connected.

FIG. 5 to FIG. 12 show various examples of partial bonding pattern at the interface 100 between the bottom side 16' and the masking layer 70. The interface has a front side 101, a back side 102 and two longitudinally-extending edges 103. The front side 101 is the side that is oriented toward the front of the article. The masking layer and the bottom side may have the same size in the longitudinal and transversal direction, in which case the interface 100 is of the same size as these layers, or one of the layers may be smaller than the other in one or both directions, in which case the interface corresponds to the common surface between both layers. Typically the masking layer may be smaller than the bottom side, so that the interface has the same surface as the masking layer. For example the masking layer 70 may have the same width but a shorter length that the bottom side of the core wrap 16'. The masking layer 70 may also be smaller in length and smaller in width than the bottom side.

The bonded portion 110-114 can be typically obtained by gluing with an adhesive and is represented in shading in the FIGS. 5-12. Any commercially available construction adhesive suitable for hygienic products may of course be used. The adhesive may be applied via contact applicator (typically slot glue) or non-contact applicator (for example as a spiral glue pattern). As is known in the art, the adhesive will be typically applied in slots or spirals in the longitudinal direction. The adhesive may be applied on any of the two layers but it may be advantageous to apply the adhesive on the masking layer first as the absorbent core may be less homogenous and uneven due to the presence of the absorbent material. While glue is the simplest way to attach two layers over relatively large areas, any other bonding means such point bonding such as ultrasonic bonding or fusion bonding may also be used.

Figure 13:
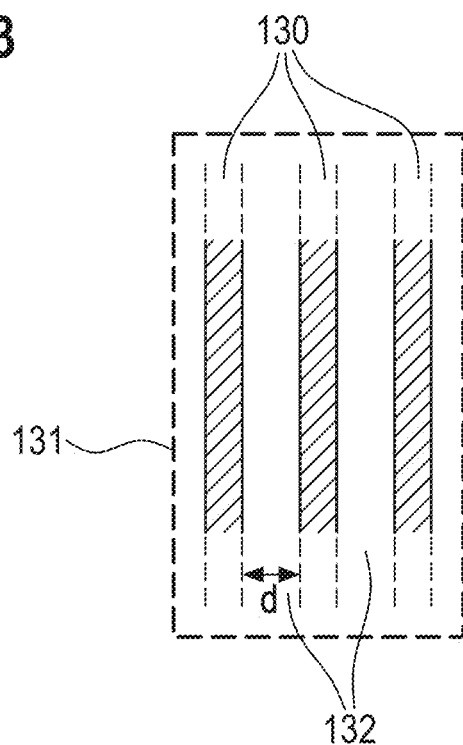
FIG. 13 schematically shows a series of adhesive slots.
Figure 14:
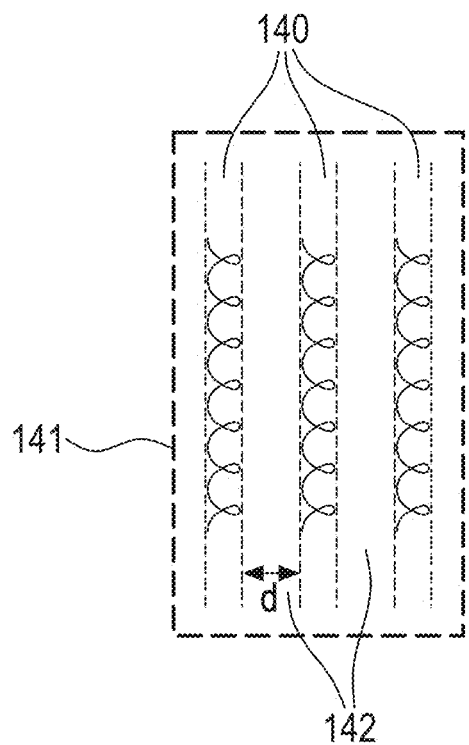
FIG. 14 schematically shows a series of adhesive spirals.

Slot gluing can comprise a single wide continuous slot or coating, or it can alternatively comprise a plurality of stripes having a width of 1 mm (or more) separated by glue-free gaps having a width of about 1 mm (or more). Spiral gluing also typically comprises several spiral adhesive rows which may be overlapping or may be separated by a small distance in the mm range, as well as of course having small glue free areas within and between each loops of the spiral row. These stripes or rows are typically longitudinally orientated as they applied in machine direction. Adjacent slots and spiral rows are considered to be part of the same bonded zone for the purpose of the invention if they are separated by a gap distance d not exceeding 20 mm (d<=20 mm). This is illustrated in FIG. 13 for a series of longitudinally-extending adhesive slots 130 separated from each other by a gap 132. If the width of the gap d is less than or equal to 20 mm, then the whole area 131 formed by the slots and the gaps is considered a bonded zone. FIG. 14 illustrates likewise for a series of longitudinally-extending spirals 140. In addition to the longitudinally-extending bands delimited by each spiral 140, the whole area 141 formed by the spirals and the gaps 142 between the spirals are considered a bonded zone 141, as long as the width of the gaps d is equal or less than 20 mm. Likewise if point bonds (spot bonds) are used, which is not typical, an area of the interface comprising point bonds separated by less than 20 mm is considered as part of the same bonded zone. An unbonded zone between two bonded zones preferably has a minimum dimension of at least 20 mm in the transversal direction and longitudinal direction.

The bonded portion is advantageously sufficiently large so that the masking layer is still efficiently anchored to the absorbent core, so that the masking layer cannot completely detach from the core wrap lower layer during manufacture and use of the absorbent article. According to the invention, the bonded portion represents from 3% to 80% of the surface of the interface of the two layers, preferably from 10% to 50% of the surface of the interface of the two layers. In the unbonded portion 120 on the other hand, the masking layer can at least partially decouple from the absorbent core during wear of the article. By avoiding an intimate contact between the layers in the unbonded portion, the masking layer can better isolate the wet absorbent core from the backsheet and also reduce the transversal stiffness in the crotch area of the article. This will now be illustrated in the examples as shown in the Figures.

Figure 5:
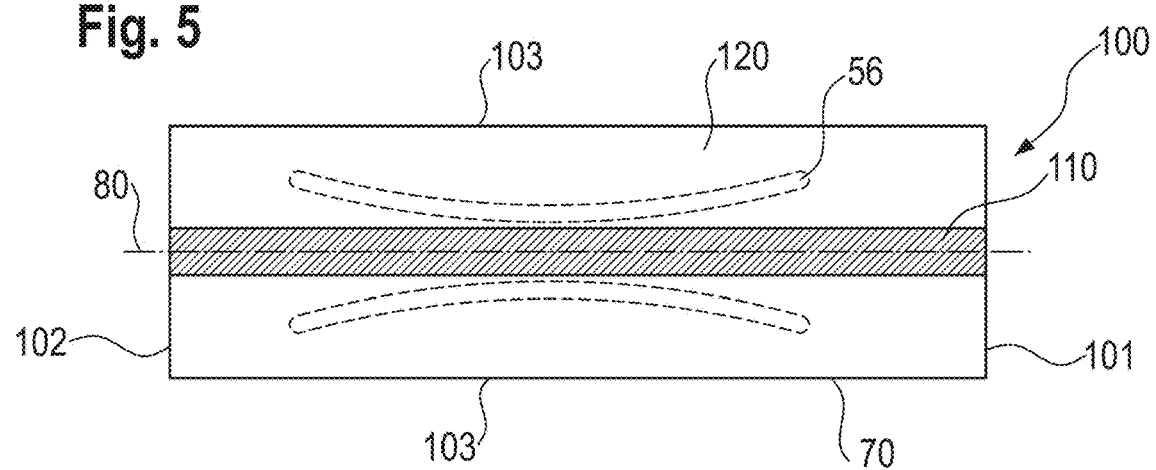
FIG. 5 shows the masking layer and a bonding portion with the core wrap consisting of a longitudinally-extending single stripe, and the outline of the channel-forming areas.
Figure 6:
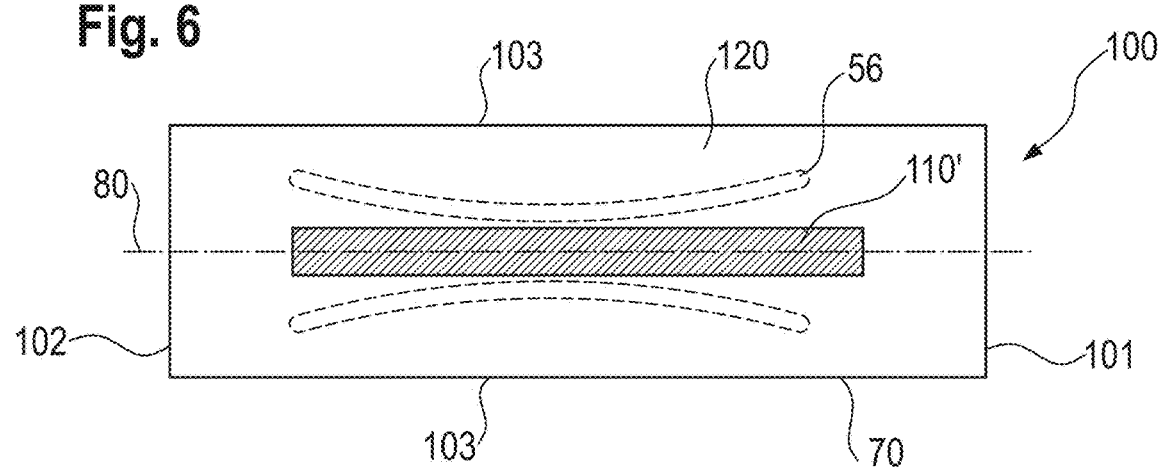

FIG. 5 shows a first example where the bonded portion comprises a single longitudinally-extending stripe 110, which is disposed on the longitudinal centerline 80 of the article. The longitudinally-extending stripe 110 may extend along the whole length of the interface, as shown in FIG. 5. The unbonded portion 120 in this example comprises an unbonded zone on one side of the longitudinally-extending stripe 110 and another unbonded zone on the other side of the bonded portion. Having a longitudinally-extending bond zone 110 disposed on the longitudinal centerline 80 of the article allows a strong anchoring of the masking layer to the absorbent core, while keeping two relatively large unbonded zones forming the unbonded portion 120 where both layers are decoupled. The longitudinally-extending stripe 110 may also be shorter at the front and/or back edge of the interface. FIG. 6 shows a variation of the example of FIG. 5, wherein the longitudinally-extending bond zone 110' does not extend to the transversal edges 101, 102 of the interface 100. The central longitudinally-extending bond zone 100, 110' may for example have a width of from 10 mm to 30 mm, for example 20 mm.

Figure 7:
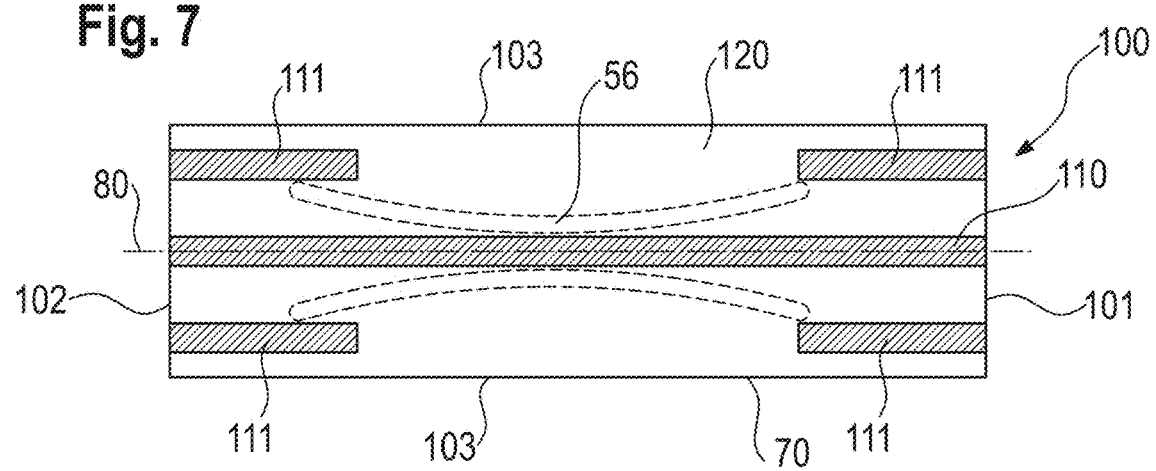

FIG. 7 shows a bonding pattern further comprising four corner bond zones 111 disposed adjacent all four corners of the interface 100 in addition to a longitudinally-extending bonded zone 110. The term "adjacent" as used herein "means in contact with or at a maximum distance of 10 mm from". It may be advantageous in some applications to have the masking layer and the core wrap bottom side bonded in one, two, three or all four of these corner bond zones 111 to avoid any flipping over of the masking layer in any these corner areas during high speed manufacture. The corner bond area 111 may be optionally placed at a distance of from about 5 mm to about 10 mm of the longitudinal edges of the masking layer (which are typically the same as longitudinal side edges 103 of the interface) to take into account any cross-direction variation during the manufacture of the article.

Figure 8:
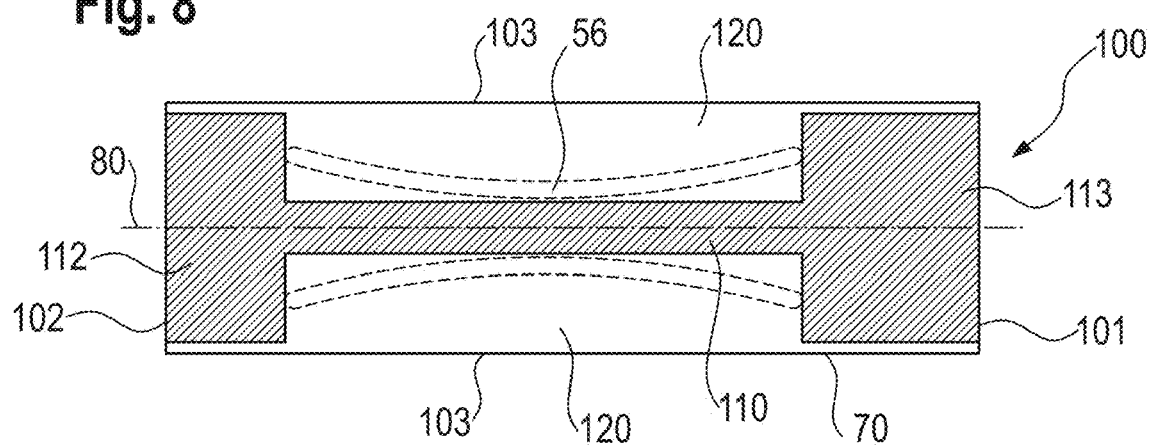
Figure 9:
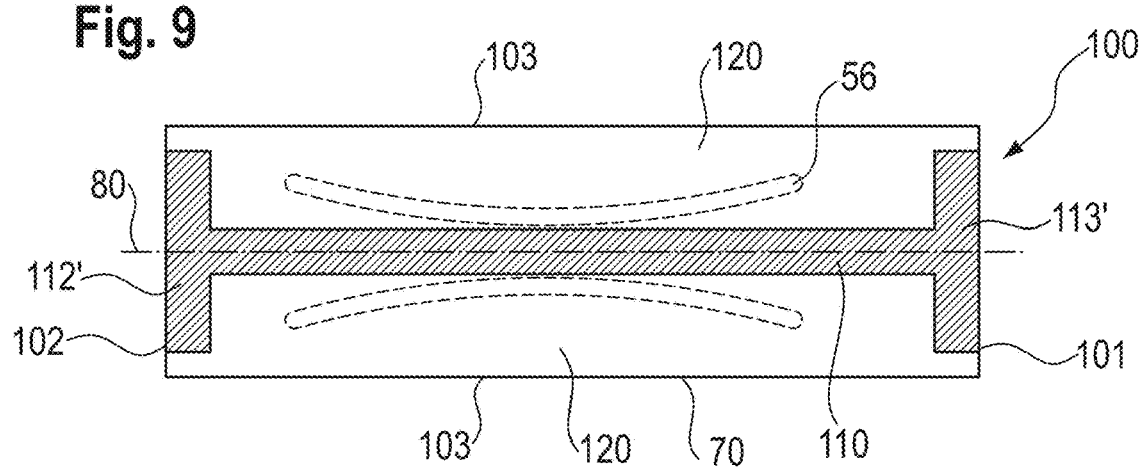

FIG. 8 and FIG. 9 show two examples of bonded portion comprising transversally extending bond zone 113, 112 disposed at the front edge 101 and back edge 102 of the interface 100 respectively. These transversally extending bond zones may be formed at both the front edge and back edge of the masking layer, for simplicity of production, so that the glue application is continuous between two consecutive masking layers. It is also possible that such a transversally extending bond zone may be only provided at, or adjacent to, only one of the front edge or the back edge of the interface or masking layer. The transversally extending bond zone 112, 113 may extend along the whole width of the transversal edges of the interface, but they may be typically shorter by a few mm than the transversal edge but still larger than the central bond zone 110, as illustrated in FIGS. 8-9, again to take into account CD variation during the making process. The function of these transversally extending side bonding area is similar to the corner bond zones of FIG. 7, i.e. they provide a more secure bonding of the two layers, in particular avoiding any corner flipping over during manufacture.

The interface 100 may be advantageously substantially free of bonding in the crotch region of the article between the channel-forming area (when present) and the closest longitudinally-extending side edges 103 of the interface 100. In particular, at least 50%, or at least 60%, or at least 70%, or more of the area between the channel-forming area and the closest longitudinally-extending side edges 103 may be free of bonding. On the other hand, when a longitudinally-extending lateral bonding zone 114 is present laterally outward of the channel-forming area in the crotch region of the article, as illustrated in FIG. 10, the transversal distance (D) between the bonding zone and the channel-forming area is advantageously of at least 10 mm.

Figure 10:
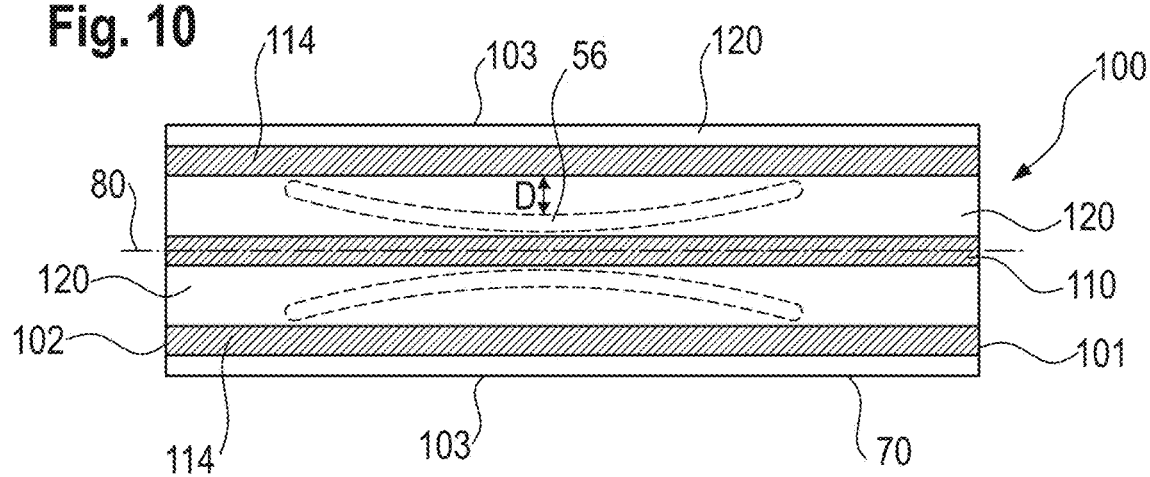

FIG. 10 illustrates an alternative bonding pattern comprising a longitudinally-extending central bond zone 110 and two longitudinally-extending lateral bond zones 114 disposed on each side of the central bond zone 110. These lateral bond zones may be adjacent (in particular at a distance of 10 mm or less) to the respective longitudinal side edges 103 of the interface. In the presence of such longitudinally-extending lateral bond zones, it may be advantageous that the maximal transversal distance D between the lateral bond zones 114 and the channel-forming areas 56 is of at least 10 mm, preferably at least 15 mm, or at least 20 mm, so that these lateral bond zones do not pull the intermediate layer into the three dimensional channels 58 when the absorbent layer swells around the channel-forming areas (as in FIG. 21).

All the FIGS. 5-10 have been illustrated with the outlines of two discrete curved channel-forming areas 56. The channel-forming areas 56 can also of course have any shape and are not necessarily curved as shown. For example the channel-forming area(s) 56 may also be straight and longitudinally-extending as shown in FIG. 11. The two channel-forming areas may also be joined at one of their extremities, e.g. forming a U or V shape as illustrated in FIG. 12, or at both of their extremities, e.g. forming an O or peanut shape.

According to the present invention, it is advantageous that the one or more channel-forming areas 56 are at least partially in the unbonded portion 120, so that the three-dimensional channels 58 are at least partially decoupled from the masking layer. The channel-forming area(s) may have at least 50% of their length, preferably at least 60% or 70% or 80% and up to 100%, as illustrated in FIGS. 5-12, within the unbonded portion 120, that is outside any of the bonding area 110-114 forming the bonded portion of the interface. As indicated previously, some overlap between the channel-forming areas 56 and the bonded portion is however possible, for example at the extremities of the channel-forming areas, along the longitudinal centerline if two channels are joined through the bonding portion, for example as illustrated in FIG. 12 to form a U shape. The length of the channel-forming area is measured along the center of their outline, which may be curvilinear or straight. In particular, the article may comprise at least two channel-forming areas disposed on each side of the longitudinal centerline, with the bonded zone 110 disposed in-between these channel-forming areas.

Figure 21:
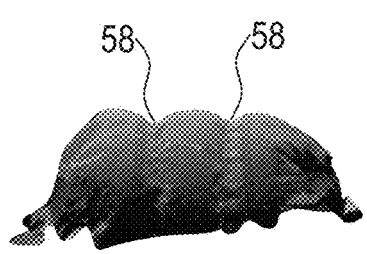
FIG. 21 shows the appearance of the crotch portion of a comparative diaper after liquid absorption.
Figure 22:
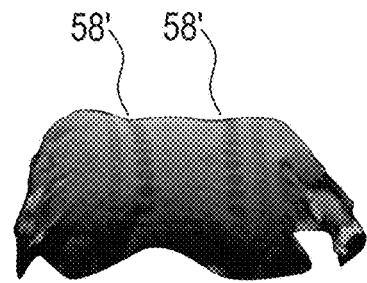
FIG. 22 shows the appearance of a diaper according to the invention in the same conditions as for FIG. 21.

An example of this core channel masking effect is illustrated in FIG. 21 and FIG. 22. Both diapers were similarly constructed, in particular have the same masking layer material according to Option 2 (disclosed above), the masking layer having substantially the same dimension as the absorbent core. Both diapers have a full glue bonding pattern between the masking layer and the backsheet (similar to FIG. 2 and FIG. 17). The diaper of FIG. 21 had a full bonding pattern at the interface between masking layer and core wrap. On the other hand, the diaper of FIG. 22 has a partial bonding having a roman I glue pattern on the wearer-facing side of the masking layer comprising a central longitudinally-extending central bonding zone and two transversal edge zones (similar to FIG. 9).

FIG. 21-22 show a picture of the crotch portion of the backsheet of these diapers, taken 5 minutes after loading with 120 ml of saline solution. In the comparative example (FIG. 21), the two curved channels 58 are highly visible at the surface of the backsheet, and the backsheet follows closely the shape of the channels. On the other hand, in the invention example shown in FIG. 22, the two channels 58', while present, are much less visible that in the comparative diaper of FIG. 21.

Masking Layer to Backsheet Attachment

Figure 17:
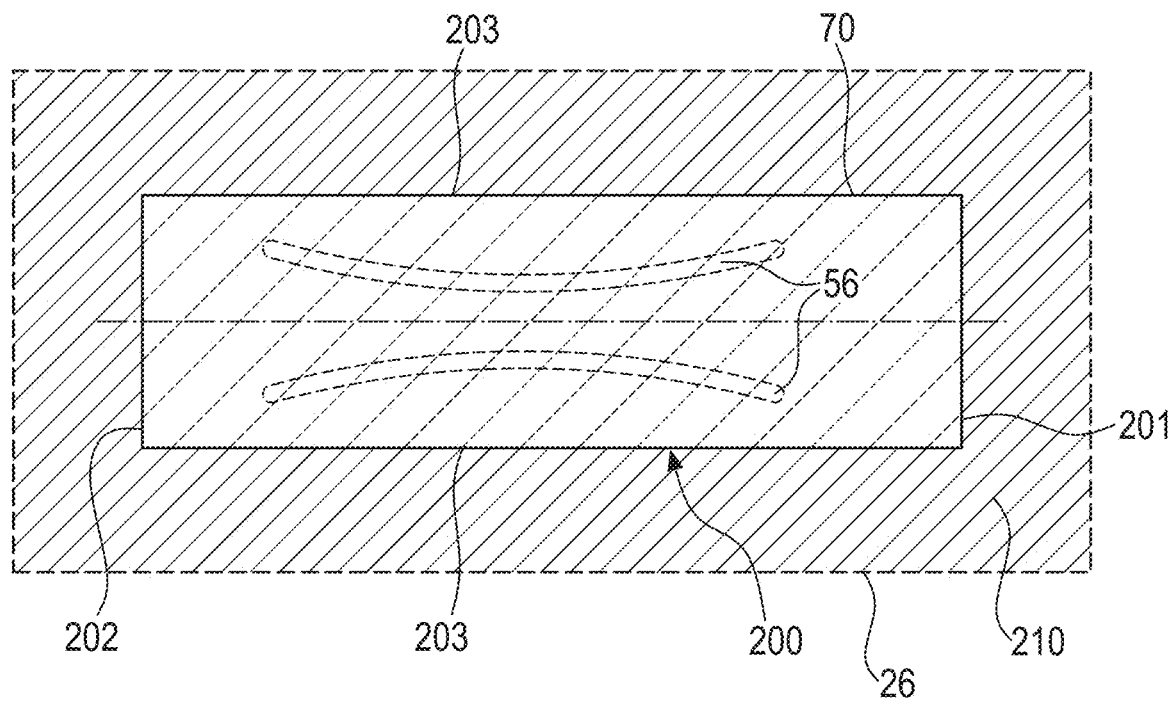
FIGS. 17-20 show the masking layer superposed with a portion of the backsheet and different bonding pattern between these two layers, with the position of the channel-forming areas in the absorbent core also shown.

The masking layer 70 is typically smaller than the backsheet 26. The garment-facing side of the masking layer faces the wearer-facing side of the backsheet. The common surface 200 between these two layers is thus typically defined by the side of the masking layer 70 oriented towards the backsheet 26. The masking layer 70 is advantageously bonded to the backsheet 26 at their interface 200 by an adhesive 210, or any other bonding means. The bonding at the second interface 200 may be a substantially full bonding as shown in FIG. 17 (similarly to FIG. 2). FIGS. 17-20 show the masking layer 70 superposed over the backsheet 26, with the outline of the channel-forming areas 56 indicated for reference, although these optional channels are of course present in the absorbent layer which is not shown in FIGS. 17-20. FIG. 17 shows the masking layer 70 fully glued to the backsheet 26 at their interface 200. Typically, at least 50%, or at least 60% or at least 70%, and up to 90% or 100% of their common surface (which as indicated typically corresponds to the garment-facing side of the masking layer 70) may be bonded to the backsheet 26. Bonding of 50% or more of the masking layer to the backsheet prevents folding or flipping of this material during production or wearing of the absorbent article and maximize the benefit of isolation of the wetness on the absorbent core from the backsheet.

Figure 18:
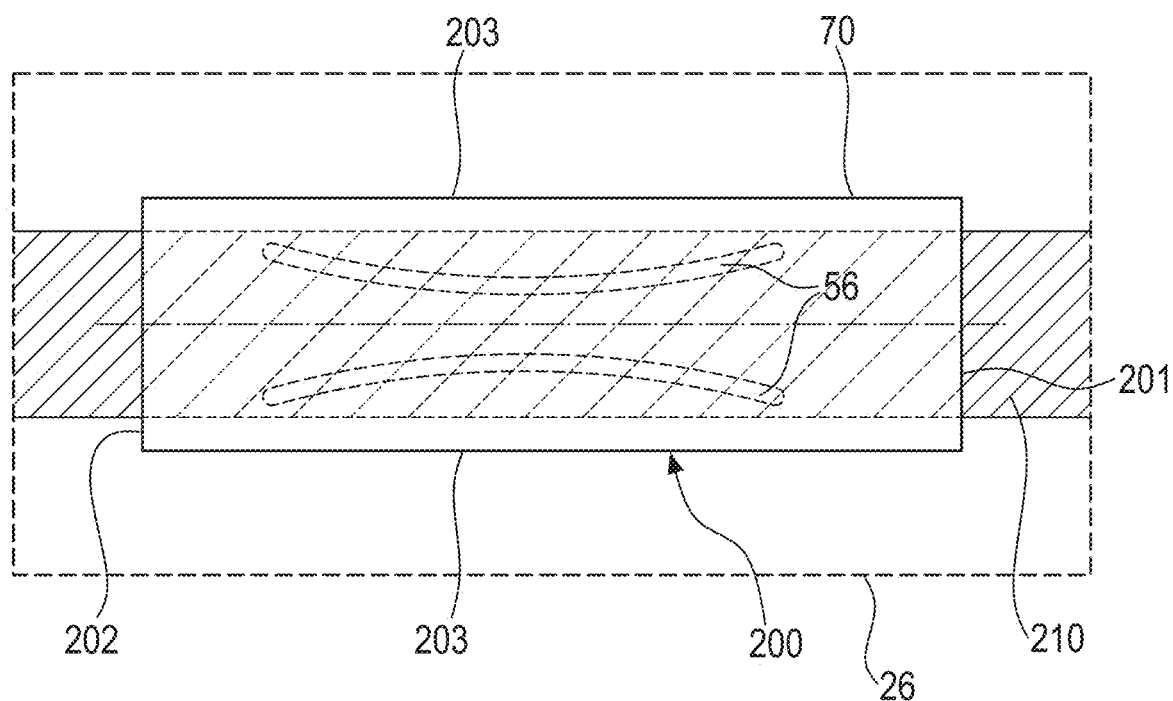
Figure 19:
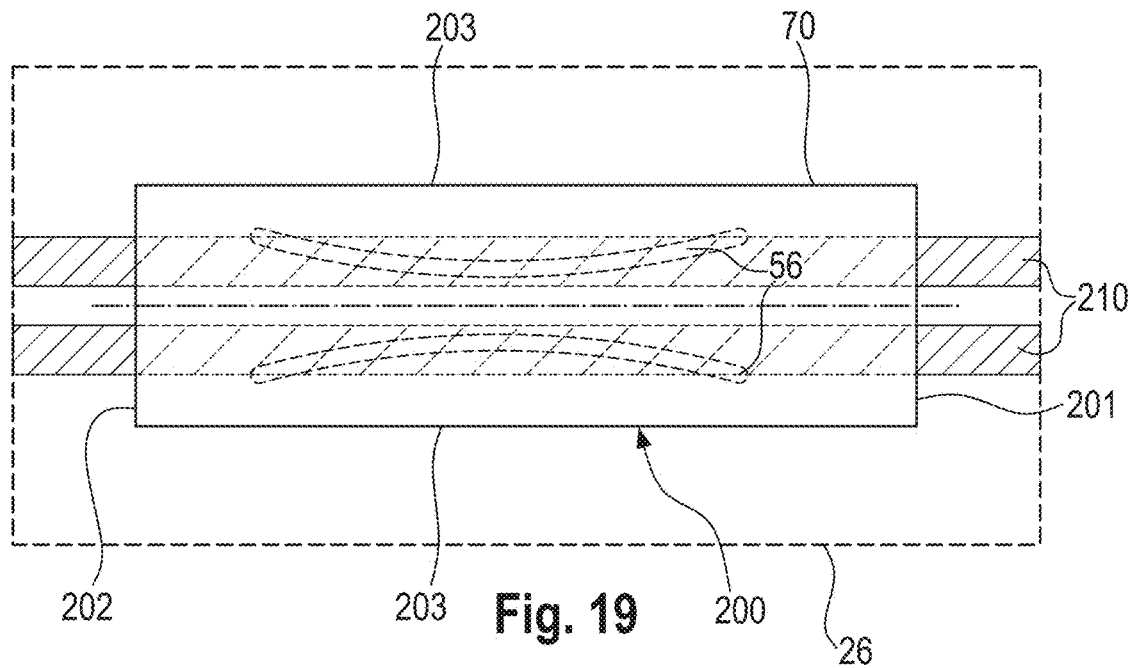
Figure 20:
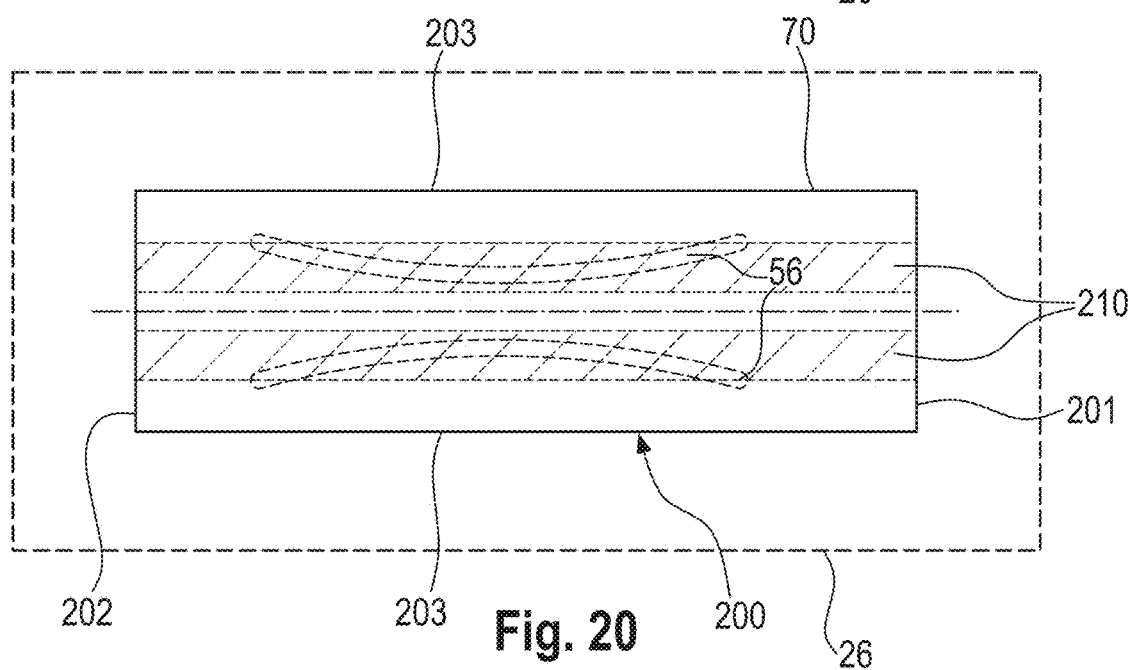

However it is also possible to only partially glue or attach the masking layer to the backsheet according to a bonding pattern comprising a bonding portion and an unbonded portion. This is illustrated in FIG. 18-20. FIG. 18 shows a bonding pattern comprising a single longitudinally-extending stripe of glue forming the bonding portion 210 that is less wide than the masking layer 70. FIG. 19 shows a bonding pattern comprising two longitudinally-extending glue stripes 210, one disposed on each side of the longitudinal axis and separated by a gap. FIG. 20 shows a similar bonding pattern as in FIG. 19, with the two longitudinal stripes not extending beyond the intermediate layer. In another bonding pattern, not represented, the bonded portion comprises a longitudinally-extending stripe overlapping with the longitudinal axis of the article and which may extend along the whole length of the masking layer and beyond towards the front and back of the article, and two transversally extending stripes at the front and back of the interface (roman I numeral pattern).

The masking layer 70 may be advantageously at least partially bonded to the backsheet 26 in the region corresponding vertically to the channel-forming areas 56, so that at least 50%, or at least 60%, or at least 70%, and up to 100% or 90% of the channel-forming areas correspond to the bonded portion 210 at the second interface 200. This may help preventing that the masking layer decouples from the backsheet when the three-dimensional channels 58 form as the absorbent material swells. In this way, the channels can become even less visible on the garment-facing side of the article, which may be a further benefit.

Bonding Pattern Examples

The relative properties of a masking layer attached to a bottom layer by different partial bonding patterns according to the invention was measured compared to a full bonding pattern. A commercially sourced diaper (Pampers® Ichiban diaper, Size 2, in China) was used for this experiment. The absorbent core comprised a pair of curved longitudinally-extending channel-forming areas 56 disposed symmetrically across the longitudinal centerline. The chassis comprised of topsheet, (upper) acquisition and distribution layers, absorbent core and backsheet was obtained by carefully removing the barrier cuffs from the commercial diapers. The backsheet was further carefully removed from the absorbent core using an ice-spray.

A masking layer was then added to the absorbent article as described as follows. The masking layer was a carded air through bonded nonwoven web made of 100% polyethylene/PET solid round bicomponent (core/sheath) staple fibers of 4.4 dtex with a basis weight of 60 g/m² corresponding to option 2 as indicated above. The masking layer had a width of 90 mm and the same length as the absorbent core.

For each diaper, the masking layer was first attached to the wearer-facing side of the backsheet with a hotmelt adhesive applied in form of spirals with a basis weight of 5 g/m² and covering the entire surface of the masking layer. The masking layer was centered in the transverse direction relative to the backsheet and aligned longitudinally with the position of the absorbent core relative to the backsheet.

Figures 15, 16:
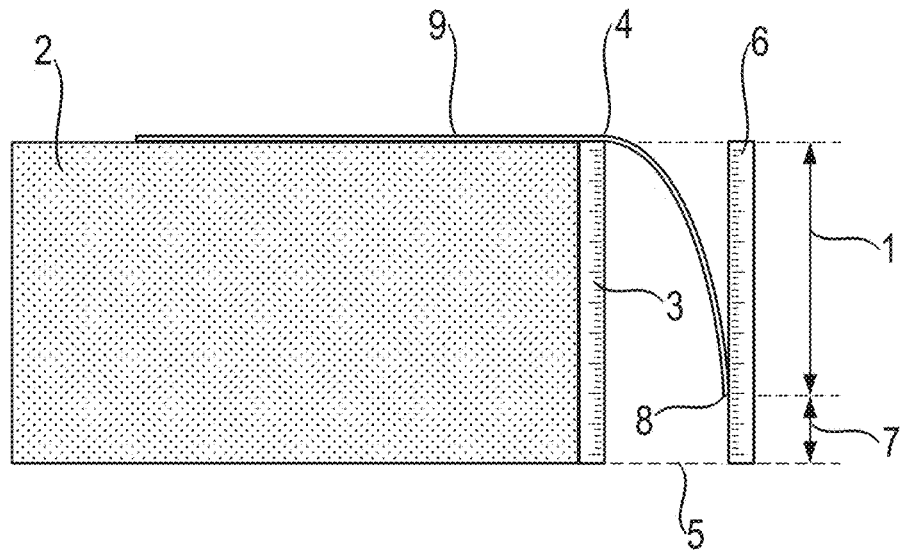
FIG. 15 shows a schematic setup for conducting the Horizontal Bending Drop Test.
FIG. 16 shows the different bonding patterns that were measured in the Stiffness Measurement section below.

The absorbent core (together with the rest of the chassis) was then attached to the other side of the masking layer with a hotmelt adhesive applied in form of a series of 10 mm wide spiral rows with a basis weight of 5 g/m² on this side of the masking layer. The melt adhesive was applied with a full coverage between the absorbent core and the masking layer for the comparative example 1, or followed a specific bonding pattern for the inventive examples 2-7. The bonding patterns used for the different examples are schematically shown in FIG. 16 and further detailed below. The glue coverage is expressed as the percentage of the interface (in this case, the same surface as the masking layer) where the spiral glue was applied. The rest of the chassis Comparative example 1 had a 100% glue coverage.

Example 2 had a 22% glue coverage, consisting of a 20 mm wide, center stripe longitudinally-extending along the full length of the masking layer.

Example 3 had a 22% glue coverage, consisting of 2 stripes of 10 mm width each disposed along the longitudinal edges of the masking layer and longitudinally-extending along the full length of the masking layer.

Example 4 had a 15% glue coverage, consisting of a 10 mm wide, longitudinally-extending center stripe and four bond corner areas (20 mm long and 10 mm wide).

Example 5 had a 16% glue coverage having a roman I numeral with a 10 mm wide longitudinally-extending stripe and a 10 mm long transversally-extending coverage across the full width of the masking layer at the front and back edges.

Example 6 had a 29% glue coverage having a roman I numeral with a 10 mm wide longitudinally-extending stripe and 40 mm long transversally-extending coverage across the full width of the masking layer at the front and back edges of the masking layer.

Example 7 had a 7% glue coverage and consisted of 5 discrete 10 mm wide, 50 mm long stripes disposed at each corner and centrally on the masking layer.

Each execution of the diaper chassis examples indicated thus obtained were then compacted in a bag at an In-Bag Stack Height (i.e. the total caliper of 10 bi-folded diapers) of 90 mm for 1 week. Then the bag was opened and the diapers taken out of the bag were conditioned at least 24 hours prior to any testing at 23° C.+/−2° C. and 50%+/−10% Relative Humidity (RH).

Stiffness Measurement

The diaper chassis thus obtained were then submitted to a crotch compression test using ProLine table-top testing machines Z005 from Zwick/Roell. For each example as described above, 6 samples were measured in a similar way. The samples were clamped on their longitudinal sides and compressed at a rate of 900 mm/minute to a maximal compression of 60 mm and then released at the same rate to the starting point. The compression force exerted by the diaper chassis was measured during the compression process. The table below shows the value measured for the first peak force for each sample (first peak force is the maximum force detected within the first 20 mm of deformation)

The table below shows the value measured for the first peak force for each sample.

|  | Example: | | | | | |
|---|---|---|---|---|---|---|
|  | 1 (comp.) | 2 | 3 | 4 | 5 | 6 | 7 |
|  | 1.5465 | 1.0170 | 0.9397 | 0.8940 | 1.0331 | 0.9233 | 0.8814 |
|  | 1.2931 | 1.1492 | 0.8116 | 0.9584 | 0.9697 | 1.1177 | 1.0287 |
|  | 1.3251 | 0.9962 | 1.0099 | 1.0599 | 1.0638 | 1.0868 | 0.8658 |
|  | 1.2681 | 1.0652 | 0.8735 | 1.0330 | 1.0764 | 0.9883 | 0.9109 |
|  | 1.2493 | 1.1957 | 0.8172 | 1.0314 | 1.0026 | 0.9882 | 0.9267 |
|  | 1.2389 | 0.9729 | 0.9190 | 0.9736 | 1.1638 | 0.9884 | 1.0069 |
| Mean | 1.32 | 1.07 | 0.90 | 0.99 | 1.05 | 1.02 | 0.94 |
| Stdev | 0.12 | 0.09 | 0.08 | 0.06 | 0.07 | 0.07 | 0.07 |

The first peak force of the inventive examples comprising a partial bonding pattern were all significantly lower than the peak force of the fully glued masking layer of comparative example 1.

TEST METHODS

All official test methods (ISO, DIN, etc.) are conducted using the latest test version available at the filing date of the application, unless otherwise indicated.

Horizontal Bending Drop at 100 mm Measurement Method

Principle: this method measures the ability of a web to bend under his own weight (sometimes designated as "drapability"). The measurement principle is to hang a length of 100 mm of the material over a sharp 90° edge and measure the vertical drop of this length of the material under its own weight, expressed in mm. This vertical drop is illustrated as reference number 1 in FIG. 11.

Apparatus: the setup for conducting the measurement is schematically shown in FIG. 11 and comprises:
 (i) a flat support box 2 made of any suitable material such as polycarbonate (e.g. Lexan®) about 400 mm long, about 200 mm wide and a height 3 of exactly 140 mm, with at least one of its top edge 4 in the width direction having a sharp 90 degree angle. The box 1 is positioned on a suitable flat surface 5, such as a lab bench;
 (ii) a movable vertical metal ruler 6, having a stable horizontal foot, and calibrated so that its zero corresponds to the flat surface 5 on which the box is disposed. The movable vertical metal ruler is used to measure the distance 7 of the hanging edge 8 of the material specimen 9 to the flat surface.

Procedure: Measurements are performed at 23° C.±2° C. and 50%±2% RH. All samples should be kept at least 24 hours in these conditions to equilibrate before conducting the tests, unless indicated otherwise. If possible, measurements are made on the web before it is integrated in an absorbent article. If this is not possible, care should be exerted when excising the sample to not impart any contamination or distortion to the test sample layer during the removal the material from other layers (using cryogenic spray, such as Cyto-Freeze, Control Company, Houston, Texas, if needed). A rectangular material specimen 9 having a width of about 80 mm and a length of about 200 mm is cut from a roll stock of the web. The length corresponds to the longitudinal direction of the nonwoven web in the absorbent article and the width corresponds to the transverse direction of the web in the absorbent article. The method can be alternatively conducted on a material specimen having a width of about 50 mm if the web original's width is shorter than 80 mm.

The material specimen 9 is laid flat on any suitable horizontal flat surface such as a lab bench, and a line is drawn at exactly at 100 mm from the front edge 8 of the material specimen in the width direction.

The material specimen 9 is then laid on top of the support box 2 with a first side of the specimen facing up (side A). The 100 mm line drawn is precisely positioned on the sharp edge 4 with the 100 mm long portion of the material specimen hanging free from the support box 2, as illustrated on FIG. 15. The section of the sample is held flush on the horizontal side of the sharp edge if needed.

The movable ruler 6 is positioned near the front edge 8 of the hanging specimen material so that the distance 7 of the hanging front edge 8 from the flat surface 5 can be measured. Since the hanging front edge 8 may not be perfectly horizontal, the distance is measured on the two corners of the hanging front edge 8, as well as in the center of the front edge 8, and the arithmetic mean of the three values recorded to the nearest mm.

The bending drop 1 is calculated as the difference between the exact Drape box height 3 (140 mm) and the recorded vertical distance 7 of the front edge 8 to the flat surface 5, as measured with the ruler 6 from the flat surface 5. The overall procedure above is repeated on five like material specimens. The arithmetic mean of the bending drop values for the five like material specimens is reported to the nearest mm as the Side A Horizontal Bending Drop at 100 mm.

The material specimen is then turned upside down (side B now up), and the same procedure described above is performed to obtain the Side B Horizontal Bending Drop. The Horizontal Bending Drop recorded overall for the material specimen is the greater of the side A Horizontal Bending Drop and the side B Horizontal Bending Drop.

Z-Compliance Index and Percent Recovery Measurement Method

Principle: This method measures the ability of a nonwoven web to be compressed in z-direction under applied pressure and then to recover to its original caliper after removing said applied pressure.

Setup: A vertically oriented electronic caliper tester having a precision of at least 0.01 mm with a 40 mm diameter circular foot may be used. The pressure exerted by the foot on the specimen is adjustable via the addition of pre-selected weights. Measurements are made at 0.85±0.05 kPa and 15.4±0.1 kPa.

Procedure: Measurements are performed at 23° C.±2° C. and 50%±2% RH. All samples should be kept at least 24 hours in these conditions to equilibrate before conducting the tests, unless indicated otherwise. If possible, measurements are made on the lower ADS before it is integrated in an absorbent article. If this is not possible, care should be exerted when excising the sample to not impart any contamination or distortion to the test sample layer during the removal the material from other layers (using cryogenic spray, such as Cyto-Freeze, Control Company, Houston, Texas, if needed). The lower ADS specimen is cut from to a square sample with a width of about 80 mm (or alternatively in case the material is not available in the suitable size in a material specimen with a width of about 50 mm).

The square sample specimen is positioned centered under the caliper foot and the caliper at 0.85±0.05 kPa (P1) is measured and recorded to the nearest 0.01 mm (C1). Without removing the sample from the equipment, the pressure is increased to 15.4±0.1 kPa (P2) and the caliper measured and recorded to the nearest 0.01 mm (C2). The pressure may be increased by adding a suitable weight on the caliper foot. Again without moving the sample, the exerted pressure is reduced back to 0.85±0.05 kPa (for example by removing the extra weight) and the caliper measured a third time (C3) and recorded to the nearest 0.01 mm.

For the specimen being measured, the compliance index is defined as:

$$Z-\text{compliance index} = (C1-C2)/(P2-P1)$$

and is recorded to the nearest 0.1 mm³/N.

The recovery is calculated as:

$$\text{recovery} = C3/C1 * 100\%$$

expressed in percent and recorded to the nearest 0.1%.

The procedure above is conducted on five like specimens of the same nonwoven.

The arithmetic mean of the compliance index values among the five specimens is calculated and reported to the nearest 0.1 mm³/N as the Compliance Index. The arithmetic mean of percent recovery values among the five specimens is calculated and reported to the nearest 0.1% as the Percent Recovery.

Caliper Test Method

The Caliper of the masking layer is determined using this Caliper Test Method. In the Caliper Test Method, two flat, parallel surfaces are used to apply unidirectional pressure to both sides of a substrate specimen, and the resulting separation between the parallel surfaces is measured. All measurements are performed in a laboratory maintained at 23±2° C. and 50±2% relative humidity and test specimens are conditioned in this environment for at least 2 hours prior to testing.

Two parallel circular surfaces of 5.6 cm diameter are oriented horizontally. If possible, measurements are made on the masking layer before it is integrated in an absorbent article. If this is not possible, care should be exerted when excising the masking layer from the product not to impart any contamination or distortion to the test sample layer during the removal of the material from other layers (using cryogenic spray, such as Cyto-Freeze, Control Company, Houston, Texas, if needed). Five equivalent rectangular specimens are taken from the masking layer of five products such that each specimen center corresponds to the center of the masking layer and such that the length and width of each specimen is greater than 5.6 cm. A specimen is then placed between the two parallel circular surfaces so that it completely covers each of the parallel surface and such that the center of the masking layer specimen is matching with the center of the parallel circular surfaces.

The parallel surfaces are then brought together at a rate of 3.0±1.0 mm/s until a pressure of 0.3 psi (2.1 kPa) is achieved, and the separation between the plates is measured and recorded to the nearest 0.01 mm within 2 seconds. The arithmetic mean of the plate separation of the 5 individual replicate specimens is calculated and reported as the Caliper of the substrate under 2.1 kPa in units of millimeters (mm) to the nearest 0.01 mm.

One suitable example of apparatus for use in the Caliper Method is a Mitutoyo Digimatic Series 543 ID-C digital indicator (Mitutoyo America Corp., Aurora, Illinois, USA), or equivalent, fitted with a circular flat "foot" at the end of the moving shaft of the indicator gauge. The indicator is mounted on a horizontal granite base such that the shaft of the indicator gauge is oriented vertically and the plane of the circular foot is parallel to the granite base. The circular foot is sized and weighted such that the gravitational force associated with the mass of the foot and the indicator shaft together divided by the area of the circular foot constitutes 2.1 kPa (0.3 psi) of downward pressure from the circular foot on the granite base. Specimens at least as large as the circular foot are analyzed between the circular foot and granite base.

Opacity Test Method

Opacity by contrast ratio measurements are made using a 0°/45° spectrophotometer suitable for making standard CIE L*a*b* color measurements such as the Hunter ColorFlex EZ Spectrophotometer (Hunter Associates Laboratory Inc., Reston, Virginia, USA) or equivalent. The diameter of the instrument's measurement port is 30 mm. Analyses are performed in a room controlled at about 23° C.±2° C. and 50%±2% relative humidity.

The instrument is calibrated per the vender instructions using standard black and white tiles provided by the instrument vendor. After calibration, the Y value of a standard white tile is measured and compared to its true value. The specified true Y value is of the standard white tile is typically in the range of 83 to 85, and the difference from true value should be 0.5 or less. The spectrophotometer is set to use the CIE XYZ color space, with a D65 standard illumination and 10° observer.

If possible, measurements are made on the layer before it is integrated in an absorbent article. If this is not possible, care should be exerted when excising the layer from the product not to impart any contamination or distortion to the test sample layer during the removal of the material from other layers (using cryogenic spray, such as Cyto-Freeze, Control Company, Houston, Texas, if needed). Five rectangular specimens of the layer are taken such that each specimen center corresponds to the central position of the layer and such that the length and width of each specimen are greater than the smallest dimension of the head.

The layer specimen is positioned flat against the instrument with the outward facing surface toward the spectrophotometer's measurement port and the center of the layer specimen is matching with the center of the port. The specimen is further positioned such that no tears, holes or apertures are within the measurement port. The white standard tile is placed onto the opposing surface of the specimen such that it completely covers the portion of the specimen over the measurement port. A reading of XYZ values is taken, and each is recorded to the nearest 0.01. Without moving the specimen, the white plate is removed and replaced with the black standard plate. A second reading of XYZ values is taken and each is recorded to the nearest 0.01.

Opacity is calculated by dividing the Y value measured using the black tile as backing, divided by the Y value measured using the white tile as backing, then multiplying the ratio by 100.

$$\text{Opacity [\%]} = \frac{Y \text{ reading over black tile}}{Y \text{ reading over white tile}} \times 100\%$$

The five layer specimens are analyzed in this way, and the Opacity of each is recorded. The arithmetic mean of the individual specimen results is calculated and reported as the Opacity in percentage to the nearest 1%.

Air Permeability Test Method

All measurements are performed in a laboratory maintained at 23±2° C. and 50±2% relative humidity and test specimens are conditioned in this environment for at least 2 hours prior to testing.

The Air Permeability of a substrate is determined according to INDA/EDANA Nonwovens Standard Procedures NWSP 070.1.RO (15) making use of a Textest FX3300 (Textest Instruments, Schwerzenbach, Switzerland) air permeability tester or equivalent. A circular test head with an area of 20 cm² is used, and while a fixed pressure of 200 Pa is maintained across the specimen, air flow through the specimen is measured in cubic meter per square meter per minute ($m^3/m^2$/min). If possible, measurements are made on the material before it is integrated in an absorbent article. If this is not possible, care should be exerted when excising the specimen from the product not to impart any contamination or distortion to the test sample layer during the removal of the material from other layers (using cryogenic spray, such as Cyto-Freeze, Control Company, Houston, Texas, if needed). Five rectangular specimens of the material are taken such that each specimen center corresponds to the center of the material and such that the length and width of each specimen are greater than the smallest dimension of the circular head. The specimen is placed under the test head such that the center of the specimen is matching the center of the test head. The five lower specimen are analyzed in this way, and the air permeability of each is recorded in $m^3/m^2$/min to the nearest 1 $m^3/m^2$/min. The arithmetic mean of the individual specimen results is calculated and reported as the Air Permeability in units $m^3/m^2$/min to the nearest 1 $m^3/m^2$/min.

In-Bag Stack Height

The in-bag stack height of a package of absorbent articles is determined as follows: Equipment: a thickness tester with a flat, rigid horizontal sliding plate is used. The thickness tester is configured so that the horizontal sliding plate moves freely in a vertical direction with the horizontal sliding plate always maintained in a horizontal orientation directly above a flat, rigid horizontal base plate. The thickness tester includes a suitable device for measuring the gap between the horizontal sliding plate and the horizontal base plate to within +0.5 mm. The horizontal sliding plate and the horizontal base plate are larger than the surface of the absorbent article package that contacts each plate, i.e. each plate extends past the contact surface of the absorbent article package in all directions. The horizontal sliding plate exerts a downward force of 850±1 gram-force (8.34 N) on the absorbent article package, which may be achieved by placing a suitable weight on the center of the non-package-contacting top surface of the horizontal sliding plate so that the total mass of the sliding plate plus added weight is 850±1 gram.

Test Procedure: Absorbent article packages are equilibrated at 23±2° C. and 50±2% relative humidity prior to measurement. The horizontal sliding plate is raised and an absorbent article package is placed centrally under the horizontal sliding plate in such a way that the absorbent articles within the package are in a horizontal orientation. Any handle or other packaging feature on the surfaces of the package that would contact either of the plates is folded flat against the surface of the package so as to minimize their impact on the measurement. The horizontal sliding plate is lowered slowly until it contacts the top surface of the package and then released. The gap between the horizontal plates is measured to within +0.5 mm ten seconds after releasing the horizontal sliding plate. Five identical packages (same size packages and same absorbent articles counts) are measured and the arithmetic mean is reported as the package width. The "In-Bag Stack Height"=(package width/absorbent article count per stack)×10 is calculated and reported to within +0.5 mm.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

What is claimed is:

1. An absorbent article comprising:
   a liquid permeable topsheet;
   a liquid impermeable backsheet;
   an absorbent core comprising an absorbent material and a core wrap, wherein the absorbent material is sandwiched between a top side and a bottom side of the core wrap, wherein the absorbent core comprises at least one channel-forming area that is substantially free of absorbent material, and wherein the channel-forming area forms a three-dimensional channel when the absorbent material swells;
   a masking layer between the absorbent core and the backsheet, wherein the masking layer comprises an air-through bonded carded nonwoven;
   wherein a wearer-facing side of the masking layer and the bottom side of the core wrap are only partially bonded to each other, their interface thus comprising a bonded portion and an unbonded portion; and
   wherein the masking layer can decouple from the three-dimensional channel when the absorbent material swells.

2. The absorbent article of claim 1, wherein the top side and the bottom side of the core wrap are bonded to each other in the channel-forming area.

3. The absorbent article of claim 1, wherein at least 50% of the length the channel-forming area corresponds to the unbonded portion.

4. The absorbent article of claim 1, wherein the bonded portion covers from about 3% to about 80% of a surface of the interface between the bottom side of the core wrap and masking layer.

5. The absorbent article of claim 1, wherein the bonded portion comprises at least one of:
   a longitudinally extending bond zone disposed on the longitudinal centerline of the article;
   one or more corner bond zone(s) adjacent to any corners of the interface;
   one or more transversally extending bond zone(s), each of the one or more transversally extending bond zone(s) disposed adjacent to a front edge of the interface or a back edge of the interface; or
   any combinations thereof.

6. The absorbent article of claim 1, wherein the bonded portion comprises a longitudinally extending bond zone and a transversally extending bond zone, wherein the transversally extending bond zone is disposed adjacent to one of a front edge of the interface or a back edge of the interface.

7. The absorbent article of claim 1, wherein the bonded portion is adhesively bonded by adhesive slots or adhesive spirals.

8. The absorbent article of claim 1, wherein the masking layer has one of a shorter length, a shorter width, or both a shorter length and shorter width, than the bottom side of the core wrap.

9. The absorbent article of claim 1, wherein at least 50% of the surface of a garment-facing side of the masking layer is bonded to the backsheet.

10. The absorbent article of claim 1, wherein the masking layer has a basis weight ranging from about 25 g/m² to about 100 g/m².

11. An absorbent article comprising:
a liquid permeable topsheet;
a liquid impermeable backsheet;
an absorbent core comprising an absorbent material and a core wrap, wherein the absorbent material is sandwiched between a top side and a bottom side of the core wrap, wherein the absorbent core comprises at least one channel-forming area that is substantially free of absorbent material, and wherein the channel-forming area forms a three-dimensional channel when the absorbent material swells;
a masking layer between the absorbent core and the backsheet, the masking layer having a higher basis weight than the material forming the bottom side of the core wrap, wherein the masking layer comprises an air-through bonded carded nonwoven;
wherein a wearer-facing side of the masking layer and the bottom side of the core wrap are only partially bonded to each other, their interface thus comprising a bonded portion and an unbonded portion, the bonding portion covering from 5% to 50% of the surface of the interface, and wherein the masking layer can decouple from the three-dimensional channel when the absorbent material swells.

12. The absorbent article of claim 11, wherein the masking layer has a basis weight ranging from about 25 g/m² to about 100 g/m².

13. The absorbent article of claim 11, wherein the bonded portion comprises at least one of:
a longitudinally extending bond zone disposed on the longitudinal centerline of the article;
one or more corner bond zone(s) adjacent to any corners of the interface;
one or more transversally extending bond zone(s), each of the one or more transversally extending bond zone(s) disposed adjacent to a front edge of the interface or a back edge of the interface; or
any combinations thereof.

14. The absorbent article of claim 11, wherein the bonded portion comprises a longitudinally extending bond zone and a transversally extending bond zone, wherein the transversally extending bond zone is disposed adjacent to a front edge of the interface or a back edge of the interface.

15. The absorbent article of claim 11, wherein the bonded portion is adhesively bonded by adhesive slots or adhesive spirals.

16. The absorbent article of claim 11, wherein the masking layer has one of a shorter length, a shorter width, or both a shorter length and shorter width, than the bottom side of the core wrap.

17. The absorbent article of claim 11, wherein the masking layer is at least partially bonded to the backsheet in the region vertically corresponding to the channel-forming area, so that about 50% to about 100% of the length of the channel-forming area correspond to the bonded portion between a garment-facing side of the masking layer and the backsheet.

18. The absorbent article of claim 11, wherein the masking layer has one or more of the following properties:
a caliper of from 0.1 to 2.0 mm, as measured at a pressure of 2.1 kPa according to the Caliper Test Method;
a Percent Recovery of at least 40%, as measured by the Z-Compliance Index and Percent Recovery Measurement Method;
an air permeability greater than 150 m³/m²/min as measured by the Air Permeability Test;
an opacity of at least 25% as measured according to the Opacity Test method.

19. The absorbent article of claim 11, wherein the absorbent material is substantially free of cellulose fibers.

20. An absorbent article comprising:
a liquid permeable topsheet;
a liquid impermeable backsheet;
an absorbent core comprising an absorbent material and a core wrap, wherein the absorbent material is sandwiched between a top side and a bottom side of the core wrap, wherein the absorbent core comprises at least one channel-forming area that is substantially free of absorbent material, and wherein the channel-forming area forms a three-dimensional channel when the absorbent material swells;
a masking layer between the absorbent core and the backsheet, wherein the masking layer comprises an air-through bonded carded nonwoven;
wherein a wearer-facing side of the masking layer and the bottom side of the core wrap are only partially bonded to each other, their interface thus comprising a bonded portion and an unbonded portion; and
wherein the entirety of the channel-forming area corresponds to the unbonded portion.

* * * * *